US009682082B2

(12) United States Patent
Lee et al.

(10) Patent No.: US 9,682,082 B2
(45) Date of Patent: Jun. 20, 2017

(54) COMBINATIONS OF AKT AND MEK INHIBITOR COMPOUNDS, AND METHODS OF USE

(75) Inventors: Brian Lee, South San Franciso, CA (US); Kui Lin, South San Francisco, CA (US); Michelle Nannini, South San Francisco, CA (US); Elizabeth Punnoose, South San Francisco, CA (US); Deepak Sampath, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/009,320

(22) PCT Filed: Mar. 30, 2012

(86) PCT No.: PCT/US2012/031716
§ 371 (c)(1),
(2), (4) Date: Oct. 1, 2013

(87) PCT Pub. No.: WO2012/135779
PCT Pub. Date: Oct. 4, 2012

(65) Prior Publication Data
US 2014/0155372 A1 Jun. 5, 2014

Related U.S. Application Data

(60) Provisional application No. 61/471,038, filed on Apr. 1, 2011.

(51) Int. Cl.
*A61K 31/517* (2006.01)
*A61K 31/165* (2006.01)
(Continued)

(52) U.S. Cl.
CPC .......... *A61K 31/517* (2013.01); *A61K 31/165* (2013.01); *A61K 31/166* (2013.01);
(Continued)

(58) Field of Classification Search
CPC .............. A61K 31/165; A61K 31/4402; A61K 31/517; A61K 45/06; A61K 31/4523; A61K 31/166; C07D 239/70
See application file for complete search history.

(56) References Cited

U.S. PATENT DOCUMENTS 3,885,035 A    5/1975   Simpson
3,956,495 A    5/1976   Lacefield
(Continued)

FOREIGN PATENT DOCUMENTS

CN        1867543 A    11/2006
CN    101605540 A    12/2009
(Continued)

OTHER PUBLICATIONS

Exelixis Inc (Discovery, Biology, and Clinical Applications, Oct. 22-26, 2007, San Francisco, CA).*
(Continued)

*Primary Examiner* — Savitha Rao
*Assistant Examiner* — Angela Brown-Pettigrew
(74) *Attorney, Agent, or Firm* — Viksnins Harris & Padys PLLP

(57) ABSTRACT

The invention provides combinations comprising a) compound of formula I: (formula I), or a pharmaceutically acceptable salt thereof; and another agent selected from GDC-0973, PD-0325901, or a pharmaceutically acceptable salt thereof. The combinations are particularly useful for treating hyperproliferative disorders, such as cancer.

(Continued)

US 9,682,082 B2
Page 2

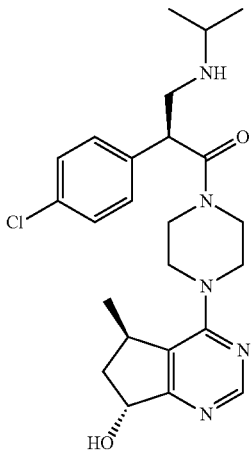

10 Claims, 32 Drawing Sheets

(51) Int. Cl.
   A61K 31/4402    (2006.01)
   A61K 45/06      (2006.01)
   C07D 239/70     (2006.01)
   A61K 31/166     (2006.01)
   A61K 31/4523    (2006.01)

(52) U.S. Cl.
   CPC ...... A61K 31/4402 (2013.01); A61K 31/4523 (2013.01); A61K 45/06 (2013.01); C07D 239/70 (2013.01)

(56) References Cited

U.S. PATENT DOCUMENTS

| | | | |
|---|---|---|---|
| 3,966,936 A | 6/1976 | Cronin et al. |
| 4,060,615 A | 11/1977 | Matier et al. |
| 4,352,928 A | 10/1982 | Hiranuma et al. |
| 4,749,704 A | 6/1988 | Iwata et al. |
| 4,871,739 A | 10/1989 | Baldwin et al. |
| 4,889,856 A | 12/1989 | Tolman et al. |
| 4,959,368 A | 9/1990 | Awaya et al. |
| 4,994,464 A | 2/1991 | Tolman et al. |
| 5,051,412 A | 9/1991 | Macor |
| 5,525,625 A | 6/1996 | Bridges et al. |
| 5,563,152 A | 10/1996 | Kulagowski et al. |
| 5,610,303 A | 3/1997 | Kimura et al. |
| 5,750,531 A | 5/1998 | Lee et al. |
| 5,750,545 A | 5/1998 | Akahoshi et al. |
| 5,817,671 A | 10/1998 | Filla et al. |
| 6,310,060 B1 | 10/2001 | Barrett et al. |
| 6,423,716 B1 | 7/2002 | Matsuno et al. |
| 6,469,004 B1 | 10/2002 | Barrett et al. |
| 6,506,798 B1 | 1/2003 | Barrett et al. |
| 6,627,628 B1 | 9/2003 | Schindler et al. |
| 6,831,175 B2 | 12/2004 | Li et al. |
| 7,041,687 B2 | 5/2006 | Binch et al. |
| 7,067,664 B1 | 6/2006 | Chen |
| 7,115,741 B2 | 10/2006 | Levy et al. |
| 7,125,880 B1 | 10/2006 | Chen |
| 7,223,738 B2 | 5/2007 | Bilodeau et al. |
| 7,223,767 B2 | 5/2007 | Clark et al. |
| 7,947,690 B2 | 5/2011 | Yonetoku et al. |
| 8,003,651 B2 | 8/2011 | Mitchell et al. |
| 8,063,050 B2 | 11/2011 | Mitchell et al. |
| 8,846,681 B2 | 9/2014 | Mitchell et al. |
| 8,853,199 B2 | 10/2014 | Mitchell et al. |
| 2003/0004193 A1 | 1/2003 | Barrett et al. |
| 2003/0045521 A1 | 3/2003 | Tecle |
| 2003/0078428 A1 | 4/2003 | Barrett et al. |
| 2003/0092748 A1 | 5/2003 | Barrett et al. |
| 2003/0199511 A1 | 10/2003 | Li et al. |
| 2003/0216460 A1 | 11/2003 | Wallace et al. |
| 2003/0232869 A1 | 12/2003 | Wallace et al. |
| 2004/0053933 A1 | 3/2004 | Pontillo et al. |
| 2004/0102360 A1 | 5/2004 | Barnett et al. |
| 2004/0116710 A1 | 6/2004 | Wallace et al. |
| 2004/0176400 A1 | 9/2004 | Capelli et al. |
| 2005/0059687 A1 | 3/2005 | Makings et al. |
| 2005/0130954 A1 | 6/2005 | Mitchell et al. |
| 2005/0182061 A1 | 8/2005 | Green et al. |
| 2006/0025074 A1 | 2/2006 | Liang et al. |
| 2006/0062400 A1 | 3/2006 | Chia-Chun |
| 2007/0004708 A1 | 1/2007 | Andreotti et al. |
| 2007/0027156 A1 | 2/2007 | Nakai et al. |
| 2007/0135466 A1 | 6/2007 | Ledeboer et al. |
| 2008/0051399 A1* | 2/2008 | Mitchell et al. ........ 514/235.2 |
| 2008/0076774 A1 | 3/2008 | Anand et al. |
| 2008/0188482 A1 | 8/2008 | Rice et al. |
| 2009/0098135 A1 | 4/2009 | Belvin et al. |
| 2010/0069357 A1 | 3/2010 | Bergeron et al. |

FOREIGN PATENT DOCUMENTS

| | | |
|---|---|---|
| EP | 194161 | 9/1986 |
| JP | 2004-512277 | 4/2004 |
| JP | 2005-521659 | 7/2005 |
| JP | 2005-525303 | 8/2005 |
| WO | WO 95/03286 | 2/1995 |
| WO | WO 98/43960 | 10/1998 |
| WO | WO 99/01421 | 1/1999 |
| WO | WO 99/01426 | 1/1999 |
| WO | WO 00/40235 | 7/2000 |
| WO | WO 00/40237 | 7/2000 |
| WO | WO 00/41505 | 7/2000 |
| WO | WO 00/41994 | 7/2000 |
| WO | WO 00/42002 | 7/2000 |
| WO | WO 00/42003 | 7/2000 |
| WO | WO 00/42022 | 7/2000 |
| WO | WO 00/42029 | 7/2000 |
| WO | WO 00/68201 | 11/2000 |
| WO | WO 01/05390 | 1/2001 |
| WO | WO 01/05391 | 1/2001 |
| WO | WO 01/05392 | 1/2001 |
| WO | WO 01/05393 | 1/2001 |
| WO | WO 01/68619 | 9/2001 |
| WO | WO 02/06213 | 1/2002 |
| WO | WO 02/18319 | 3/2002 |
| WO | WO 02/22604 | 3/2002 |
| WO | WO 02/44166 | 6/2002 |
| WO | WO 02/083139 | 10/2002 |
| WO | WO 03/022214 | 3/2003 |
| WO | WO 03/049678 | 6/2003 |
| WO | WO 03/062225 | 7/2003 |
| WO | WO 03/064397 | 8/2003 |
| WO | WO 03/077855 | 9/2003 |
| WO | WO 03/077914 | 9/2003 |
| WO | WO 03/086279 | 10/2003 |
| WO | WO 03/086394 | 10/2003 |
| WO | WO 03/086403 | 10/2003 |
| WO | WO 03/086404 | 10/2003 |
| WO | WO 03/094918 | 11/2003 |
| WO | WO 2004/041162 | 5/2004 |
| WO | WO 2004/048343 | 6/2004 |
| WO | WO 2004/096130 | 11/2004 |
| WO | WO 2005/014558 | 2/2005 |
| WO | WO 2005/105780 | 11/2005 |
| WO | WO 2005/117909 | 12/2005 |
| WO | WO 2006/000589 | 1/2006 |
| WO | WO 2006/046023 | 5/2006 |
| WO | WO 2006/071819 | 7/2006 |
| WO | WO 2006/090261 | 8/2006 |
| WO | WO 2006/094230 | 9/2006 |
| WO | WO 2006/136830 | 12/2006 |
| WO | 2007044515 A1 | 4/2007 |

(56) References Cited

FOREIGN PATENT DOCUMENTS

| WO | WO 2007/042298 | 4/2007 |
| --- | --- | --- |
| WO | WO 2007/077961 | 7/2007 |
| WO | WO 2007/125320 | 11/2007 |
| WO | WO 2008/003697 | 1/2008 |
| WO | WO 2008/003958 | 1/2008 |
| WO | WO 2008/003978 | 1/2008 |
| WO | WO 2008/005511 | 1/2008 |
| WO | WO 2008/005964 | 1/2008 |
| WO | WO 2008/006032 | 1/2008 |
| WO | WO 2008/006039 | 1/2008 |
| WO | WO 2008/006040 | 1/2008 |
| WO | WO 2008/012635 | 1/2008 |
| WO | WO 2010/006225 | 1/2010 |
| WO | WO2011/038082 | * 3/2011 |

OTHER PUBLICATIONS

Gavin Robertson (Cancer and Metastasis Reviews 24: 273-285, 2005).*

GIST Support (http://www.gistsupport.org/treatments-for-gist/emerging-treatments/inhibitors-of-pathways-downstream-of-kit-pdgfr/gdc-0973.php, accessed Dec. 5, 2014).*

Neidle's Cancer Drug Design and Discovery (Elsevier/Academic Press, 2008, pp. 427-431.*

Paraiso et al (Cancer Res; 71(7) Apr. 1, 2011).*

J.A. McCubrey et al. (Biochimica et Biophysica Acta 1773 (2007) 1263-1284).*

Blake et al., "Discovery and Preclinical Pharmacology of a Selective ATP-Competitive Akt Inhibitor (GDC-0068) for the Treatment of Human Tumors", Journal of Medicinal Chemistry, 55, 8110-8127, 2012.

Cohen, "Protein kinases—the major drug targets of the twenty-first century?" Nature Rev. Drug Discovery 1, 309-315 (2002).

Davies et al., "Catalytic Enantioselective Synthesis of β-2-Amino Acids", Angew. Chem. 114 (12), 2301-2303 (2002).

D'Souza et al., "(R)—(+)—3-Amino-2-phenylpropanoic Acid: a Revised Absolute Configureation based on an Enantioselective Synthesis and an X-Ray Crystal Structure of the Salt with (1S)—(+)—Camphor-10-sulfonic Acid", J. Chem. Soc. Perkins Trans. 1, 2 pages, (1995).

Office Action issued by the Columbian Patent Office for CL App. No. 09-010.508, and translation thereof Mar. 25, 2013 (mailing date) 14 pages.

Funke et al., "A Phase Ib/II Study Testing the Safety and Efficacy of Combined Inhibition of the PI3K/Akt and Androgen Receptor Signaling Pathways in Castration-resistant Prostate Cancer: GDC-0068 or GDC-0980 with Abiraterone Acetate Versus Abiraterone Acetate" American Society of Clinical Oncology (ASCO) Annual Meeting, Chicago, IL, Jun. 1-5, 2012, Poster TPS2616, 1 page.

Funke et al., "A Phase Ib/II Study Testing the Safety and Efficacy of Combined Inhibition of the PI3K/Akt and Androgen Receptor Signaling Pathways in Castration-resistant Prostate Cancer: GDC-0068 or GDC-0980 with Abiraterone Acetate Versus Abiraterone Acetate", J. Clin. Oncology (Meeting Abstracts), 30(suppl.), abstract: TPS2616, 3 pages, 2012.

Li, Qun "Expert Opinion: Recent Progress in the Discovery of Akt Inhibitors as Anticancer Agents", Informa Healthcare, 2007, 17(9), pp. 1077-1130.

Lin, Kui, "GDC-0068, A Novel, Selective, ATP-Competitive Inhibitor of AKT", In: Proceedings of the 102nd Annual Meeting of the American Association for Cancer Research, Apr. 2-6, 2011, Orlando, Florida, Philadelphia (PA): AACR; 2011, Presentation No. DDT02-01, 1 page abstract, and 30 pages of the corresponding presentation given Apr. 3, 2011.

Lin et al., "An ATP-Site On-Off Switch That Restricts Phosphatase Accessibility of Akt", Sci. Signal., 5(223), ra37, pp. 1-10 (2012).

Neidle, "18.3 Failure Modes in Clinical Development", Cancer Drug Design and Discovery, (Elsevier/Academic Press), pp. 427-431 (2008).

Ohno, S., et al., "Synthesis and Hypoglycemic Activity of 7,8-Dihydro-6H-thiopyrano[3,2-d]pyrimidine Derivatives and Related Compounds", Chem. Pharm. Bull., 1986, 34(10), 4150-4165.

Patent Cooperation Treaty, International Searching Authority, Search Report and Written Opinion for PCT/US2012/31716, 10 pages, Jun. 27, 2012.

Ross, L., et al., "Potential Anticancer Agents. XVIII. Synthesis of Substituted 4,5-Trimethylenepyrimidines", J. Am. Chem. Soc., 1959, 81, 3108-3113.

Saura, C., et al., "A Phase Ib Study of the Akt Inhibitor GDC-0068 with Docetaxel or mFOLFOX6 in Patients with Advanced Solid Tumors", American Society of Clinical Oncology (ASCO), Annual Meeting, Chicago, IL, Jun. 1-5, 2012, Poster 3021, 1 page.

Saura, C., et al., "A Phase Ib Study of the Akt Inhibitor GDC-0068 with Docetaxel or mFOLFOX6 in Patients with Advanced Solid Tumors", J. Clin. Oncology (Meeting Abstracts), 30(suppl.), abstract: 3021, 3 pages, 2012.

Office Action issued by the Japanese Patent Office for JP Patent Application No. 2009-518636 and translation thereof, Sep. 20, 2012 (mailing date), 8 pages.

Tabernero et al., "First-in-human phase I study evaluating the safety, pharmacokinetics (PK), and intratumor pharmacodynamics (PD) of the novel, oral, ATP-competitive Akt inhibitor GDC-0068", J. Clin. Oncol. (Meeting Abstracts), 29(15_suppl), abstract: 3022, 3 pages, 2011.

Tabernero et al., "First-in-human phase I study evaluating the safety, pharmacokinetics (PK), and intratumor pharmacodynamics (PD) of the novel, oral, ATP-competitive Akt inhibitor GDC-0068", American Society of Clinical Oncology (ASCO), Annual Meeting, Chicago, IL, Jun. 3-7, 2011, Poster 3022, 1 page.

Tabernero et al., "Targeting the PI3K-Akt-mTOR pathway with GDC-0068, a novel selective ATP competitive Akt inhibitor", 9th International Symposium on Targeted Anticancer Therapies, Paris, France, Mar. 7-9, 2011; presentation given Mar. 9, 2011, 13 pages.

Truong, T. N., "Office Action for U.S. Appl. No. 10/993,173", United States Patent and Trademark Office, Aug. 6, 2008, 8 pages.

Truong, T. N., "Office Action for U.S. Appl. No. 10/993,173", United States Patent and Trademark Office, May 26, 2009, 8 pages.

Vippagunta, S.R., (Adv. Drug. Delivery Rev., 2001, 48, pp. 3-26).

Yan et al., "A first-in-human trial of GDC-0068: A novel, oral, ATP-competitive Akt inhibitor, demonstrates robust suppression of the Akt pathway in surrogate and tumor tissues", AACR-NCI-EORTC International Conference: Molecular Targets and Cancer Therapeutics, San Francisco, CA, Nov. 12-16, Poster B154, 1 page, 2011.

Zhao, Z., et al., "Discovery of 2,3,5-trisubstituted pyridine derivatives as potent Akt1 and Akt2 dual inhibitors", Bioorg. Med. Chem. Lett., 2005, 15, 905-909.

Zhu et al., "Discovery and SAR of oxindole—pyridine-based protein kinase B/Akt inhibitors for treating cancers", Bioorganic & Medicinal Chemistry Letters, 16, 3424-3429 (2006).

Fan, "Cancer Research Fronts", Xian Jiaotong University Press, Dec. 2003, 7 pages, published on Dec. 21, 2003.

Fremin et al., "From Basic Research to Clinical Development of MEK1/2 Inhibitors for Cancer Therapy", Journal of Hematology & Oncology, vol. 3 (8), 1-11 (2010).

Nature News: Drug giants unite to develop cancer therapy, http://www.nature.com/news/2009/090602/full/news.209.536.html (Jun. 2, 2009).

Wee, et al., "PI3K pathway activation mediates resistance to MEK inhibitors in KRAS mutant cancers", Cancer Res 69 (10), 4286-4293 (2009).

Liu, et al., "Potent Inhibition of Thyroid Cancer Cells by the MEK Inhibitor PD0325901 and its Potentiation by Suppression of hte PI3K and NF-kB Pathways", Thyroid vol. 18 (8), 853-864 (2008).

* cited by examiner

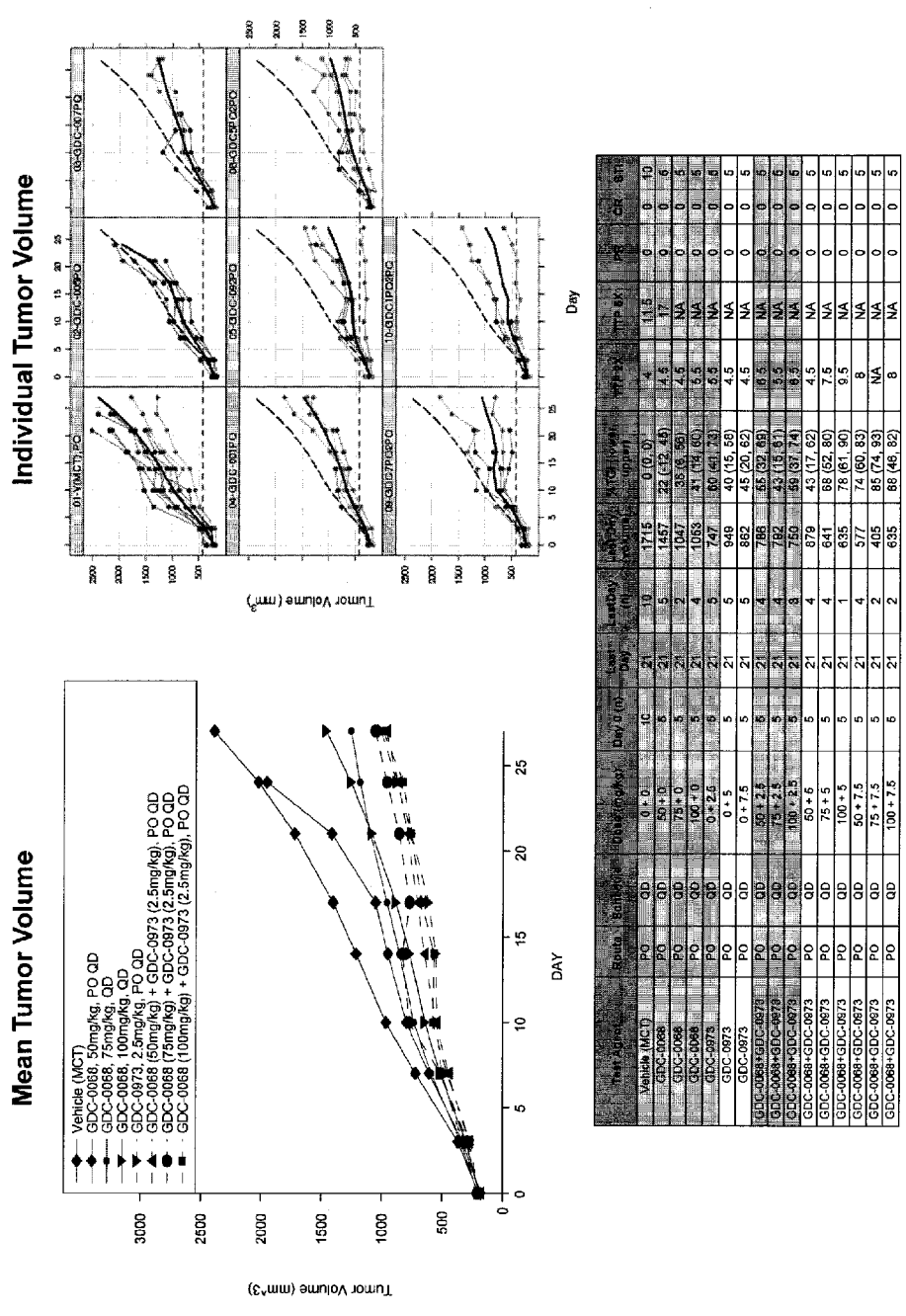
FIG 1 GDC-0068 and GDC-0973 (2.5mg/kg): Tumor Volumes

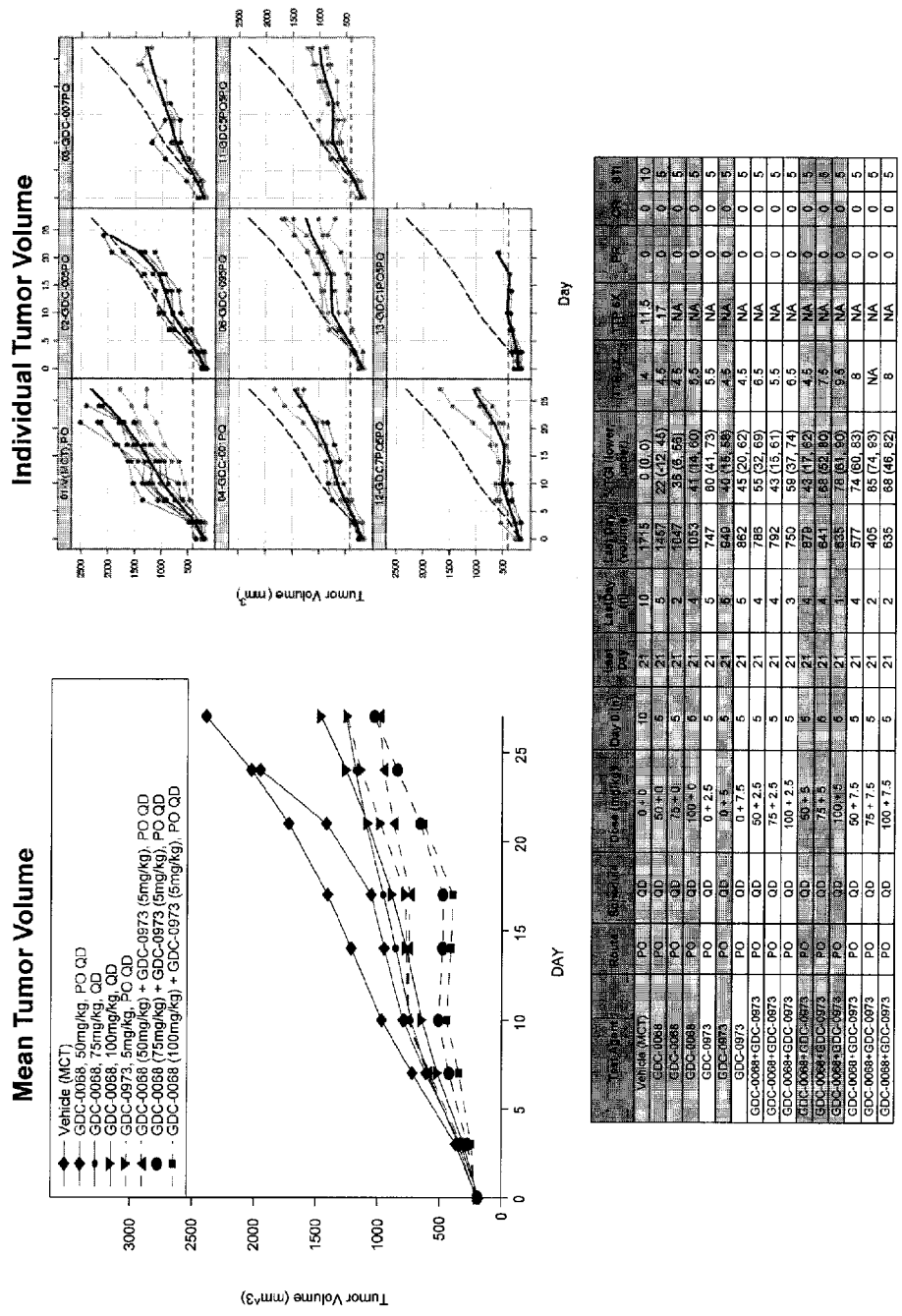
FIG 2 GDC-0068 and GDC-0973 (5mg/kg): Tumor Volumes

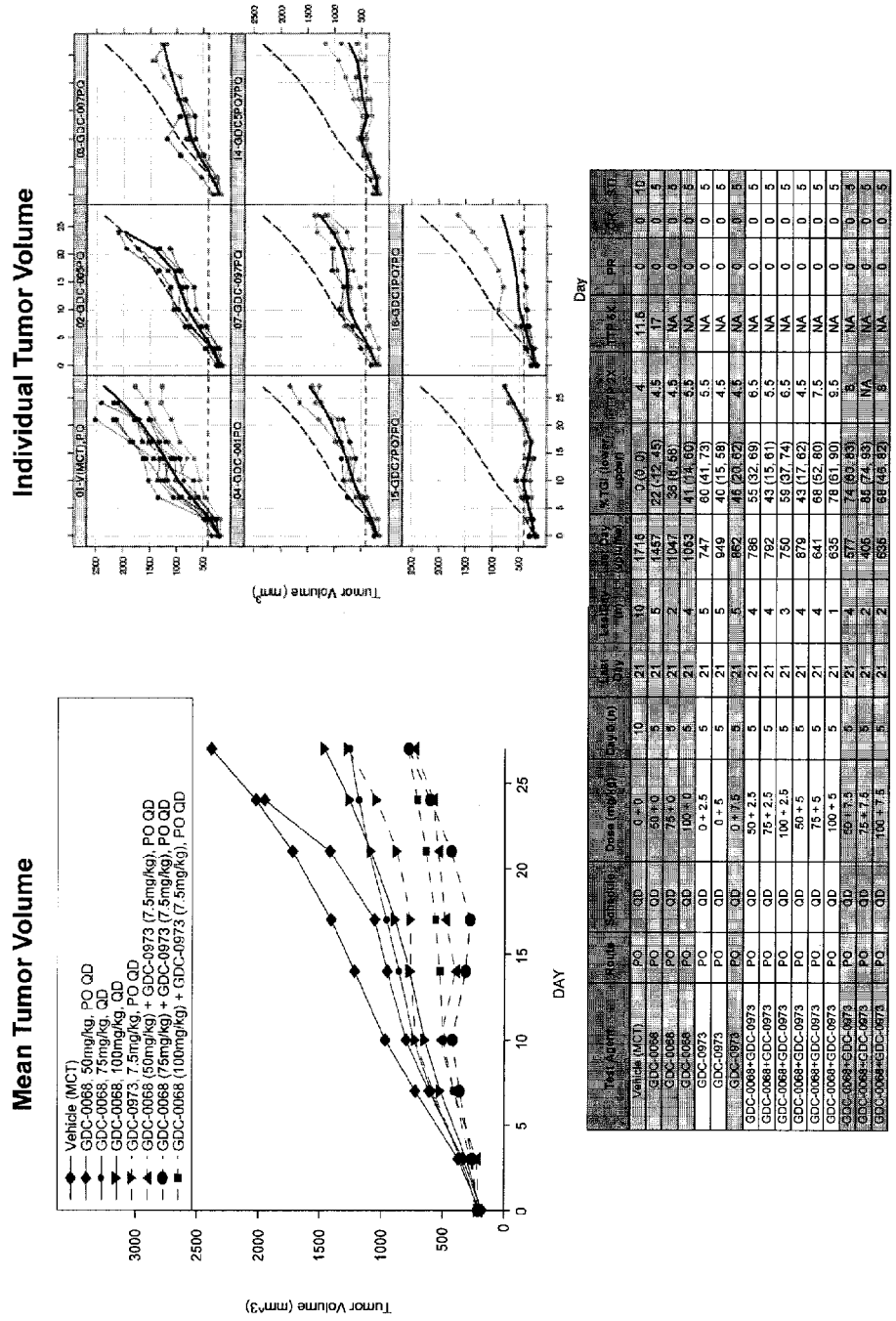
FIG 3 GDC-0068 and GDC-0973 (7.5mg/kg): Tumor Volumes

FIG 4 Colorectal Cancer in vitro

| Tissue | Cell line | Akt pathway activation | Ras/Raf activation | RTK | other | IC50s GDC-0068 | IC50s XL-518 | Bliss Scores Total Positive | Bliss Scores Total |
|---|---|---|---|---|---|---|---|---|---|
| Colon | HCT-116 (PRC)* | PI3K H1047R | Kras G13D | | E-Cad, RER+ | >10 | 0.25 | 458 | 460 |
| Colon | DLD-1 (PRC)* | PI3K E545K,D549N | Kras G13D | | p53, RER+ | >10 | 3.15 | | 339 |
| Colon | LS174T (PRC)* | PI3K H1047 | Kras G12D | | E-Cad, RER+ | 9.13 | 0.25 | | 242 |
| Colon | HM-7 | PI3K H1047 | Kras G12D | | | 7.09 | 0.57 | 228 | 140 |
| Colon | LS180 | PI3K H1047R, P421L | Kras G12D | | RER+ | >10 | 0.08 | 226 | 173 |
| Colon | HT-29 (PRC)* | PI3K L568F, L569F,P449T | Braf V600E | | p53 | >10 | 0.01 | 204 | 201 |
| Colon | SW620 (PRC)* | | Kras G12V | | RER+ | >10 | 0.11 | 199 | 156 |

| | | | | | XL518 | | |
|---|---|---|---|---|---|---|---|
| | cell line | molecular subtype | PI3K activation | MAPK activation | GDC-0068 IC50 (uM) | Run1 6/29/2009 | Run2 7/10/2009 | Run3 8/17/2009 |
| CRC | KM12 | | PTEN- | | 2.3 | | | |
| CRC | LOVO | | AKT2 mut | KRAS | 2.25 | | | |
| CRC | LS180 | | PI3K Mut | KRAS | max | | s | |
| CRC | MDST8 | | PTEN- | BRAF | max | | s | |
| CRC | HT-29 | | PI3K Mut | BRAF | max | | | |

- High frequency of coexisting PI3K and Ras pathway mutations
- Strong synergy seen in cells with both pathway mutations

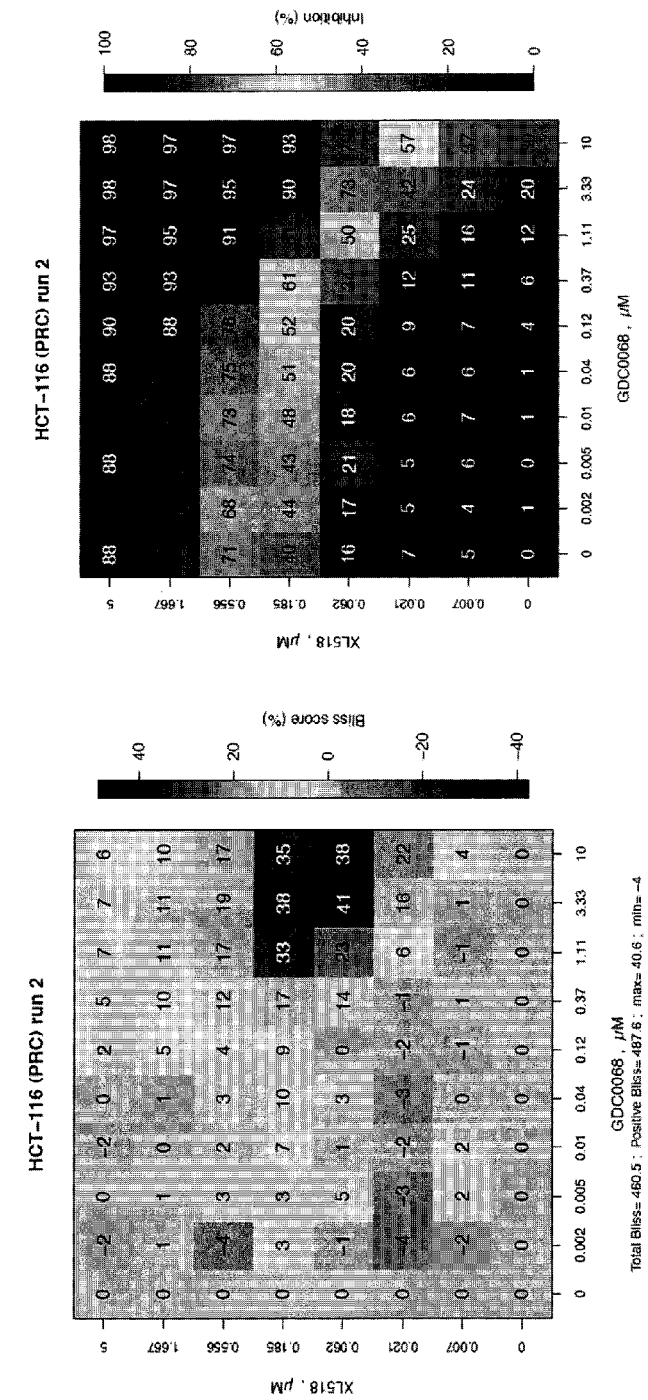
FIG 5 HCT-116 (Colon - PI3K and Kras Mutant) In Vitro Combination of Mek and Akt
Bliss Score Range: GDC-0973 0.021-0.185uM, GDC-0068 0.37-10uM

FIG 6 NSCLC

| Tissue | Cell line | Akt pathway activation | Ras/Raf activation | RTK | other | IC50s GDC-0068 | IC50s XL-518 | Bliss Scores Total Positive | Bliss Scores Total |
|---|---|---|---|---|---|---|---|---|---|
| Lung-NSCLC | H460 (PRC)* | PI3K E545K | Kras Q61H | EGFR L933P | LKB1 | >10 | >5 | 545 | 468 |
| Lung-NSCLC | NCI-H2122 | | Kras G12C | | p53, LKB1 | >10 | 0.3 | | 496 |
| Lung-NSCLC | H1299 (PRC)* | | Nras Q61K | | p53 | >10 | 3.01 | | 384 |
| Lung-NSCLC | SK-MES-1 (PRC)* | PI3K L997P | Kras N85K | | p53 | >10 | 0.50 | | 277 |
| Lung-NSCLC | MV522 (PRC)* | | Braf V600E | | | >10 | 0.04 | | 125 |
| Lung-NSCLC | A549 (PRC)* | PI3K M772X, N996H | Kras G12S | | p53, LKB1 | >10 | 0.34 | | 180 |
| B Lymphoblast | NCI-BL2122 | | | | | 4.54 | >5 | 12 | -549 |

| | cell line | molecular subtype | PI3K activation | MAPK activation | GDC-0068 IC50 (uM) | XL518 Run1 6/29/2009 | XL518 Run2 7/10/2009 | XL518 Run3 8/17/2009 |
|---|---|---|---|---|---|---|---|---|
| NSCLC | NCI-H2122 | | WT | KRAS | max | s | s | s |
| NSCLC | NCI-H460 | | PI3K mut | KRAS | max | s | s | s |

- High frequency of coexisting PI3K and Ras pathway mutations
- Strong synergy seen in all cells tested—including cells with Ras/Raf mutations alone with no known PI3K pathway mutations

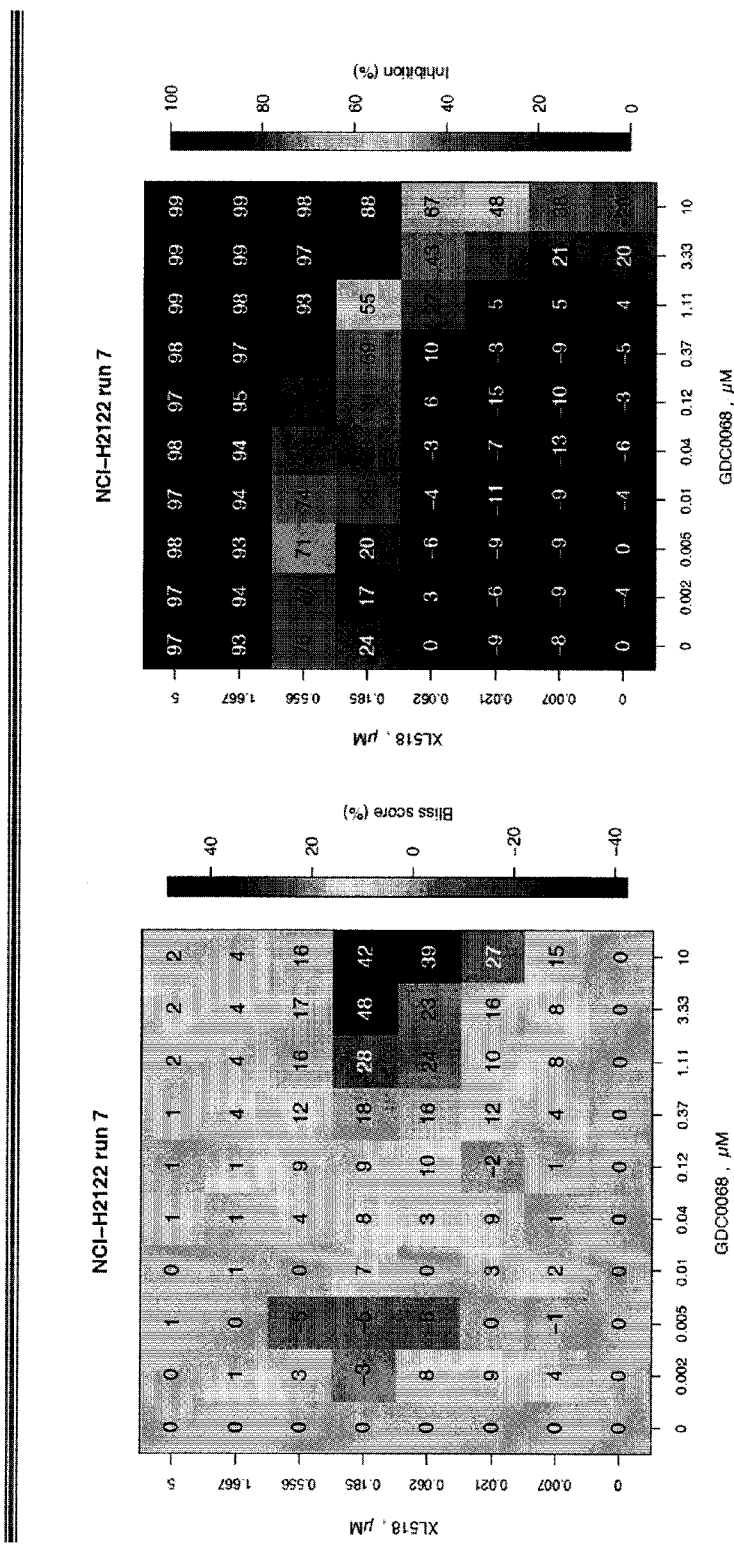
FIG 7 H2122 (NSCLC - Kras Mutant) In Vitro Combination of Mek and Akt
Bliss Score Range: GDC-0973 0.021-0.185uM, GDC-0068 0.37-10uM

FIG 8 Melanoma

| Tissue | Cell line | Akt pathway activation | Ras/Raf activation | RTK | other | IC50s GDC-0068 | IC50s XL-518 | Bliss Scores Total Positive | Bliss Scores Total |
|---|---|---|---|---|---|---|---|---|---|
| Melanoma | MALME3M | | Braf V600E | | | >10 | 0.07 | 719 | 684 |
| Melanoma | A375 | Akt3 hi | Braf V600E | | | >10 | 0.01 | 553 | 548 |
| Melanoma | A2058 | PTEN- | Braf V600E | | p53 | >10 | 0.6 | 502 | 446 |
| Melanoma | 537MEL | PTEN- | Braf del,amp | | | 2.33 | 0.02 | 434 | 428 |
| Normal fibroblast | MALME3 | | | | | 5.02 | >5 | 42 | -142 |

- Predominantly Braf mut, often coexist with PTEN-, sometimes with PI3K mut or Akt3 overexpression
- Strong synergy seen in all melanoma cells tested—including cells with BRaf mutation alone with no known PI3K pathway mutations

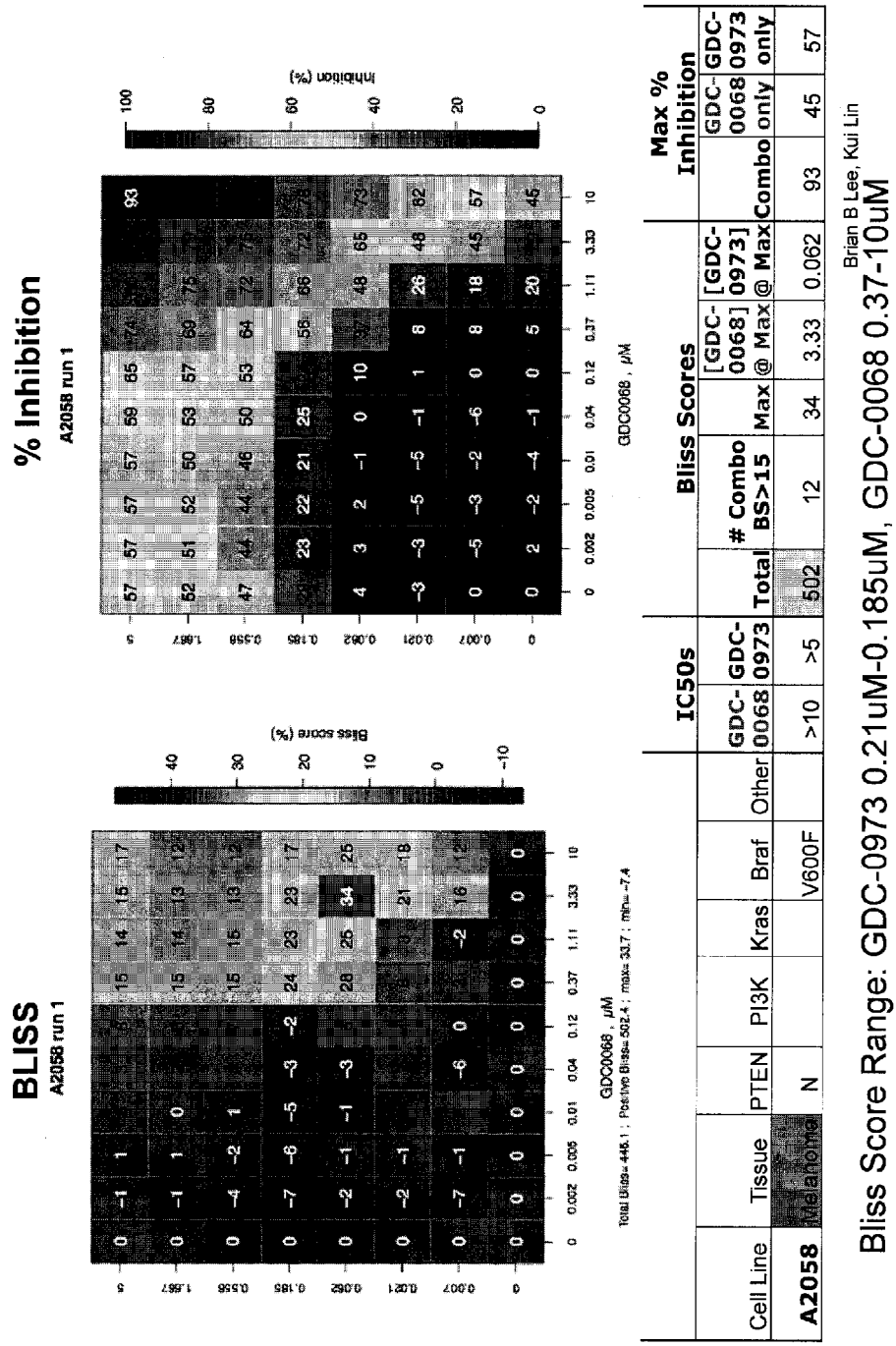
FIG 9 A2058 (Melanoma - PTEN -/- and Braf Mutant) In Vitro Combination of Mek and Akt Minimal In Vitro Single Agent Activity
Bliss Score Range: GDC-0973 0.21uM-0.185uM, GDC-0068 0.37-10uM

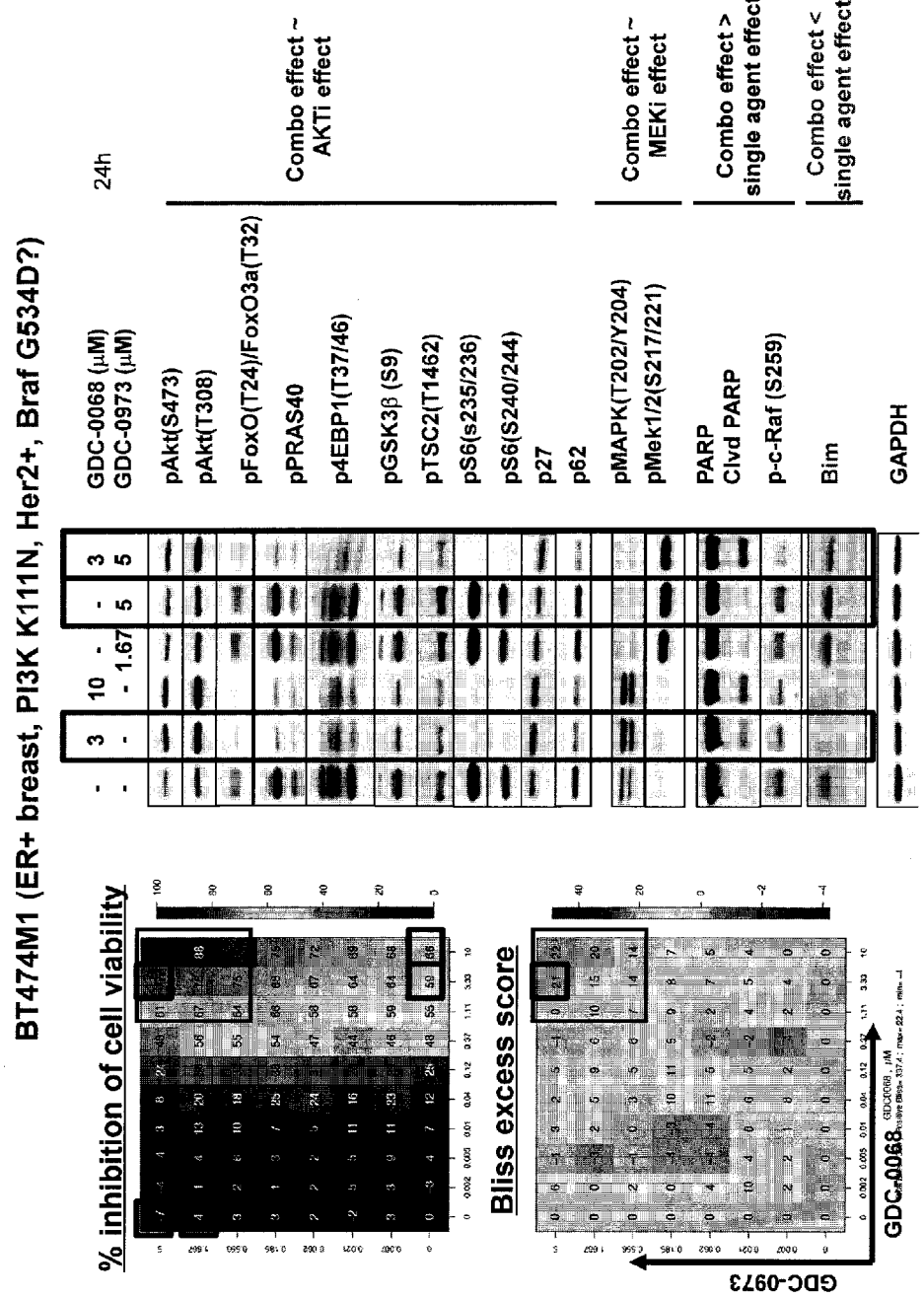
FIG 10 Enhanced knockdown of both pathway activity compared to single agents alone

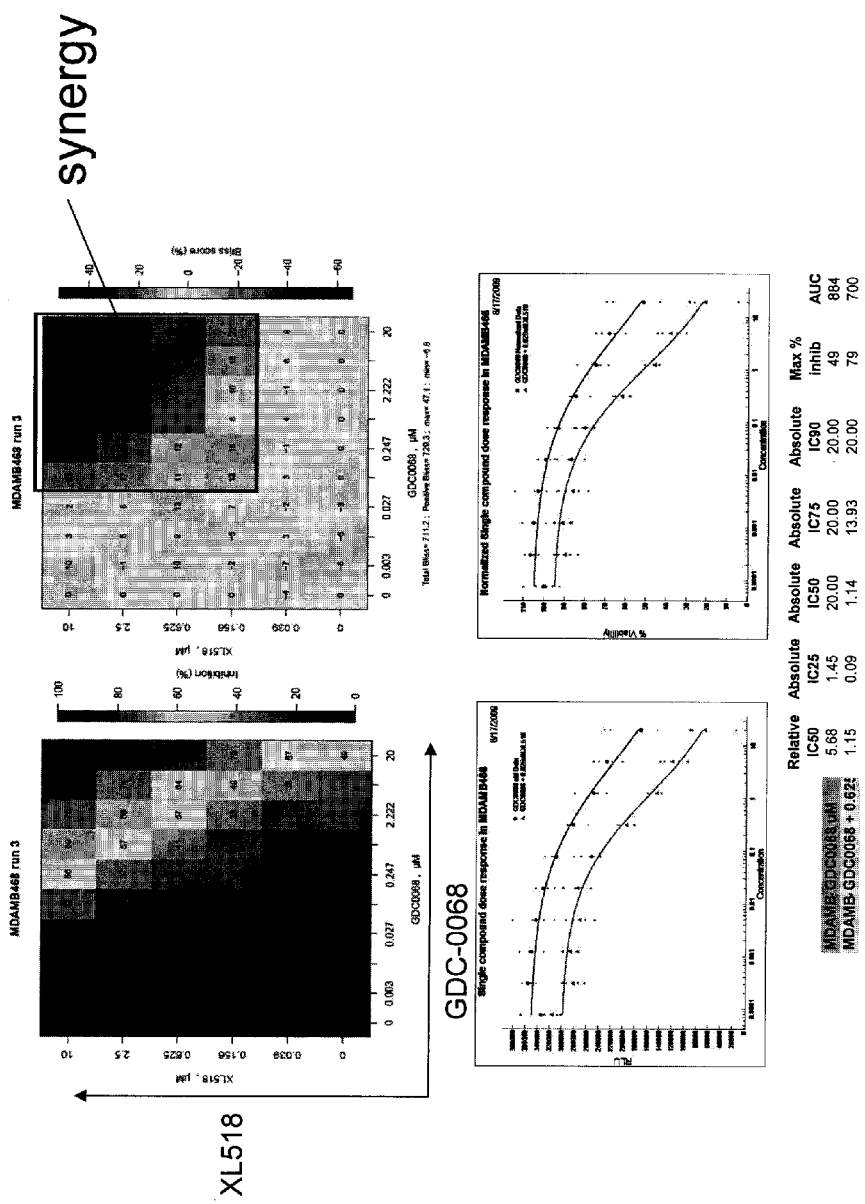
FIG 11 XL518 x GDC0068 combo – MDA-MB-468

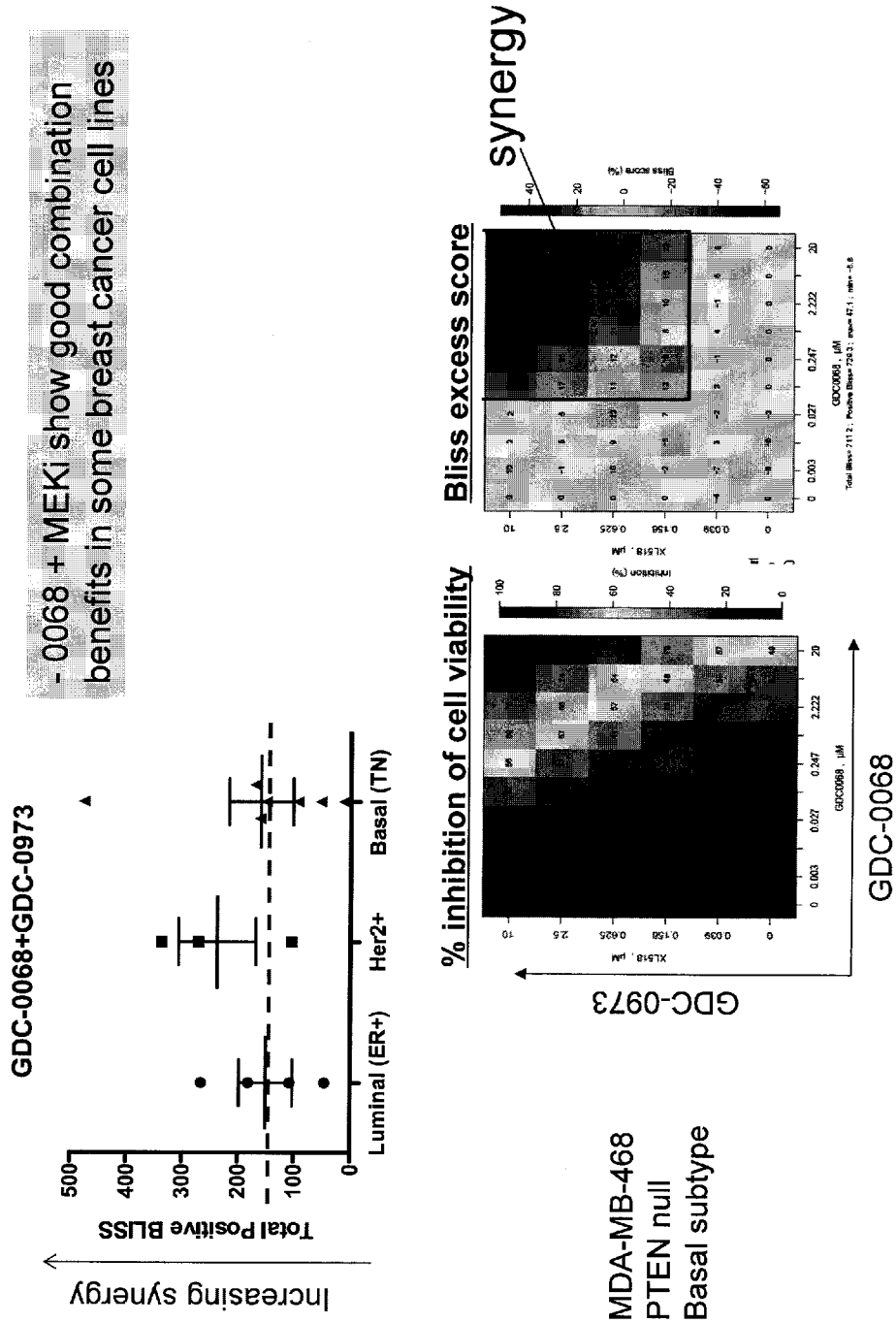
FIG 12 GDC-0973 (MEKi) + GDC0068 combination

FIG 13 Ovarian

| Tissue | Cell line | Akt pathway activation | Ras/Raf activation | RTK | other | IC50s GDC-0068 | IC50s XL-518 | Bliss Scores Total Positive | Bliss Scores Total |
|---|---|---|---|---|---|---|---|---|---|
| Ovarian | OVCAR3 | PI3Kp110amp, p85mut, Akt2amp | | | p53 | 9.04 | >5 | 575 | 573 |
| Ovarian | PEO1 | ND | ND | ND | ND | >10 | 1.81 | 334 | 334 |
| Ovarian | TOV-21G | PTEN-, PI3K H1047Y | Kras G13C | | | 0.67 | 2.48 | 358 | 282 |
| Ovarian | SK-OV-3 (PRO)* | PI3K H1047R | | | | >10 | >5 | 219 | 239 |
| Ovarian | IGROV1 | PI3K O1069W | | | p53 | 0.66 | 0.39 | 237 | 211 |
| Ovarian | A2780 (PRO)* | PTEN mut | | | p53,p16 | >10 | 0.98 | 131 | 43 |
| Ovarian | OV-90 | | Braf del | | | 9.19 | 0.39 | 107 | 47 |

| | cell line | molecular subtype PI3K activation | MAPK activation | GDC-0068 IC50 (uM) | XL518 Run1 6/29/2009 | Run2 7/10/2009 | Run3 8/17/2009 |
|---|---|---|---|---|---|---|---|
| ovarian | TOV21G | PTEN/PI3K | KRAS | 0.558 | s | | |
| ovarian | CAOV3 | PIK3CA 4 copies | | max | | | |
| ovarian | EFO27 | PTEN | | 0.55 | | | |
| ovarian | OVCAR3 | AKT2 amp | | 1.44 | | | |
| ovarian | SKOV3 | PI3K | | max | | | s |

- Low frequency of coexisting PI3K and Ras pathway mutations
- Raf-1 and A-Raf but not Braf activation have been implicated in ovarian cancers
- synergy seen in cells with no known Ras/Raf mutations, including cells resistant to GDC-0068 alone or both agents

FIG 14 Prostate

| | cell line | molecular subtype PI3K activation | MAPK activation | GDC-0068 IC50 (uM) | Run1 6/29/2009 | XL518 Run2 7/10/2009 | Run3 8/17/2009 |
|---|---|---|---|---|---|---|---|
| prostate | 22RV1 | PI3K Mut | BRAF | 9.09 | | | |
| prostate | DU145 | WT | | max | | s | |
| prostate | PC3 | PTEN- | | 2.26 | | | |
| prostate | PC3MLN4 | PTEN- | | 11.03 IC50>5 | | | |

- Low frequency of coexisting PI3K and Ras pathway mutations
- Synergy seen with a line with both PI3K and Braf mutations.

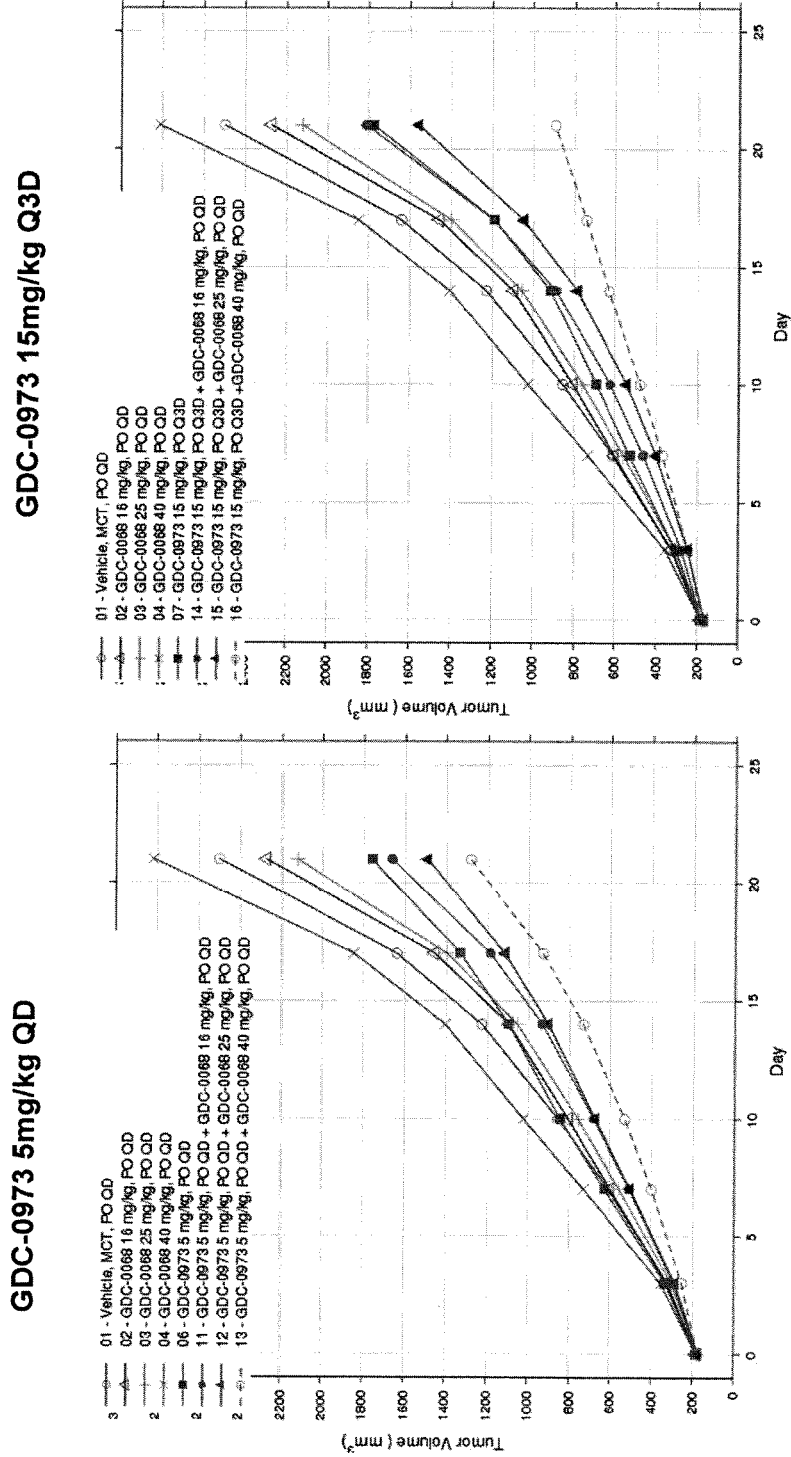
FIG 15 GDC-0068 Dosed PO + GDC-0973 (MEK inhibitor) in MX-1 Breast Tumors

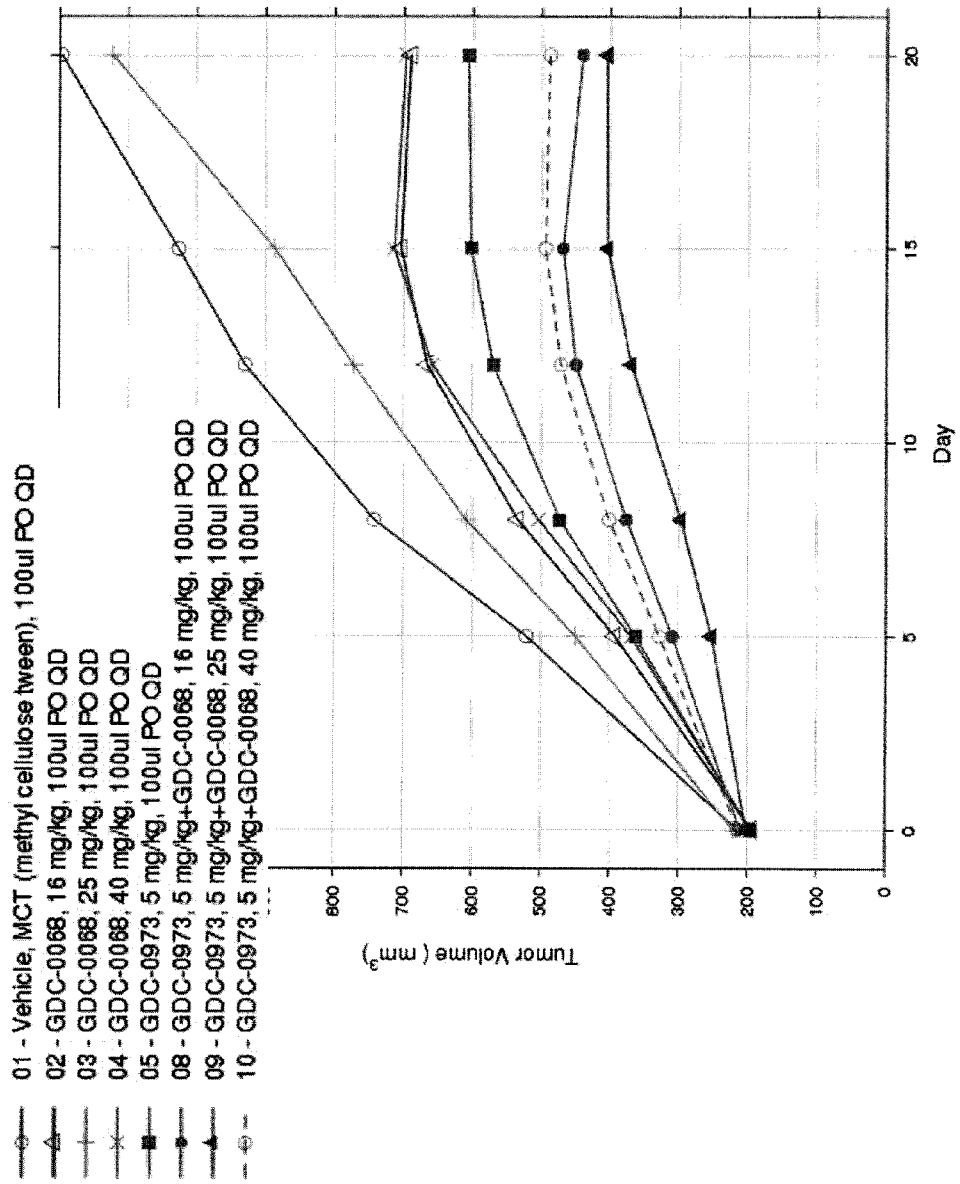

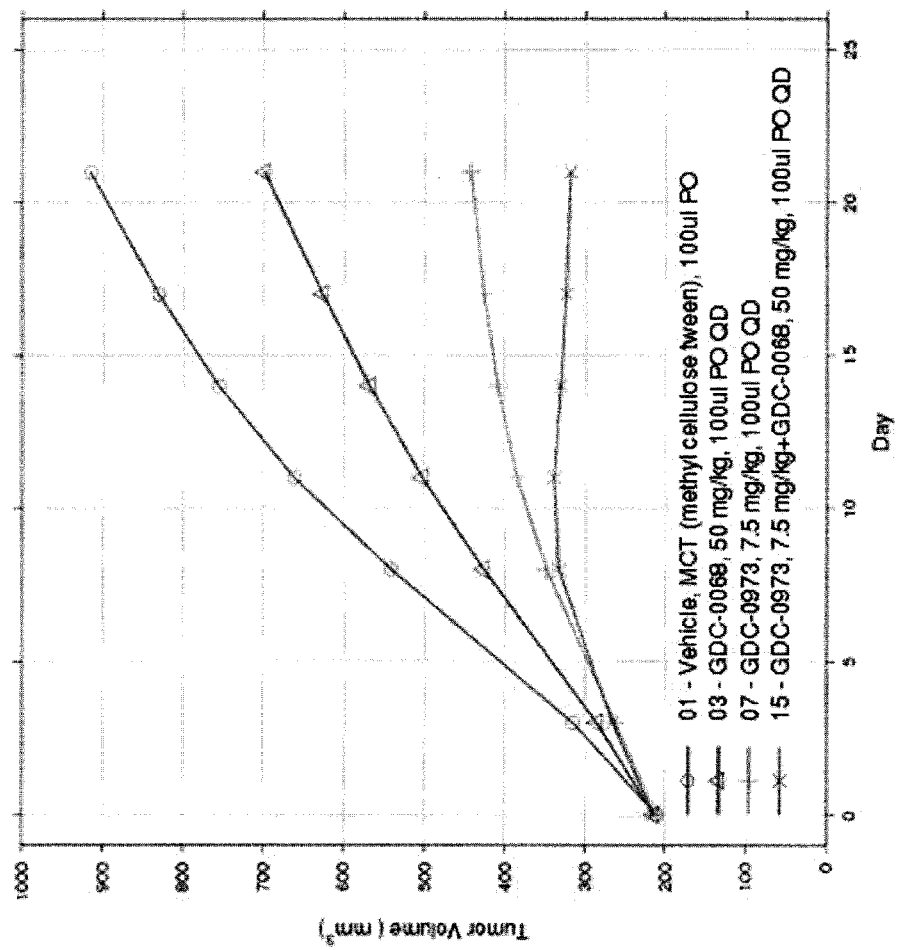
FIG 17 GDC-0068 Dosed PO + GDC-0973 (MEK inhibitor) in SW1990 Pancreatic Tumors

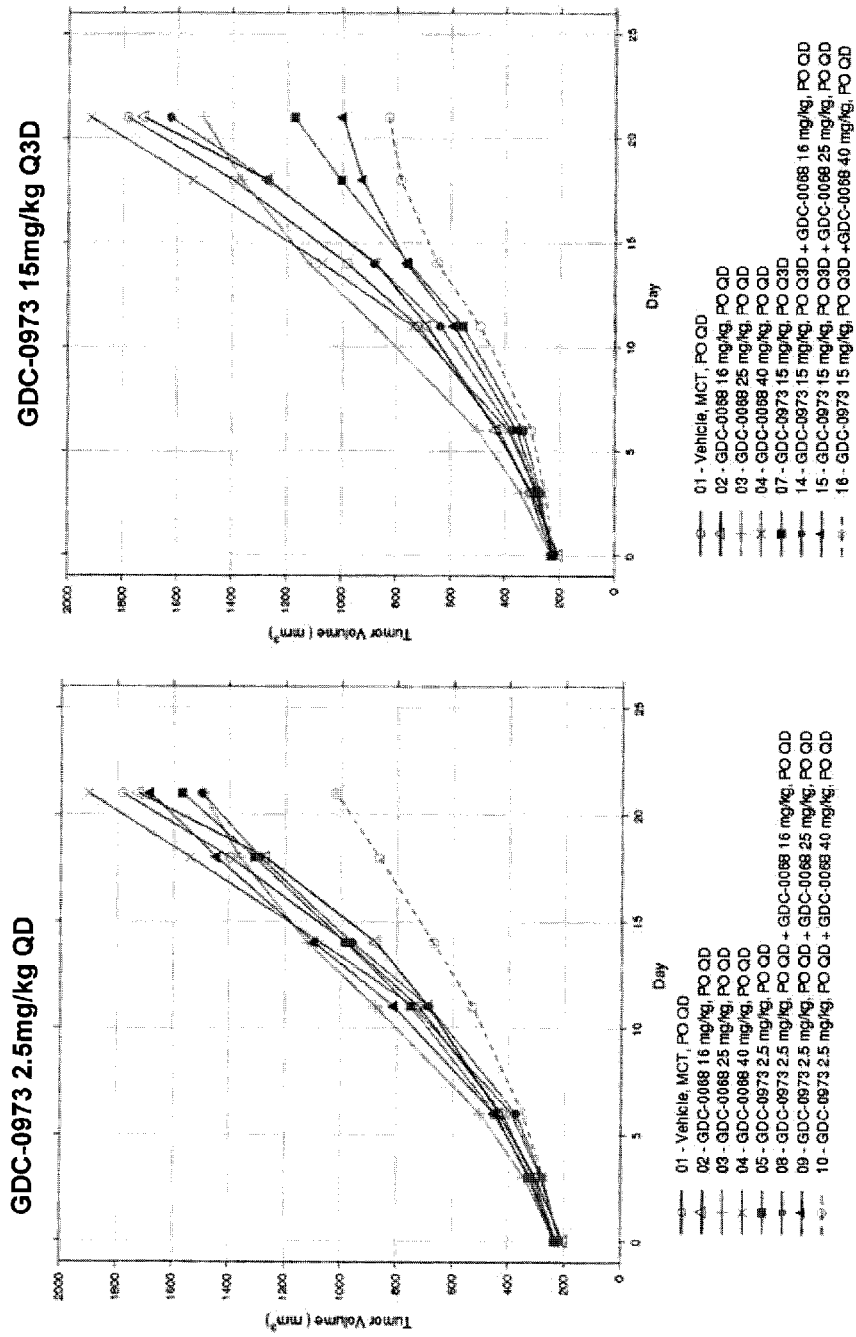
FIG 18 GDC-0068 Dosed PO + GDC-0973 (MEK inhibitor) in Pa_Tu-8902 Pancreatic Tumors

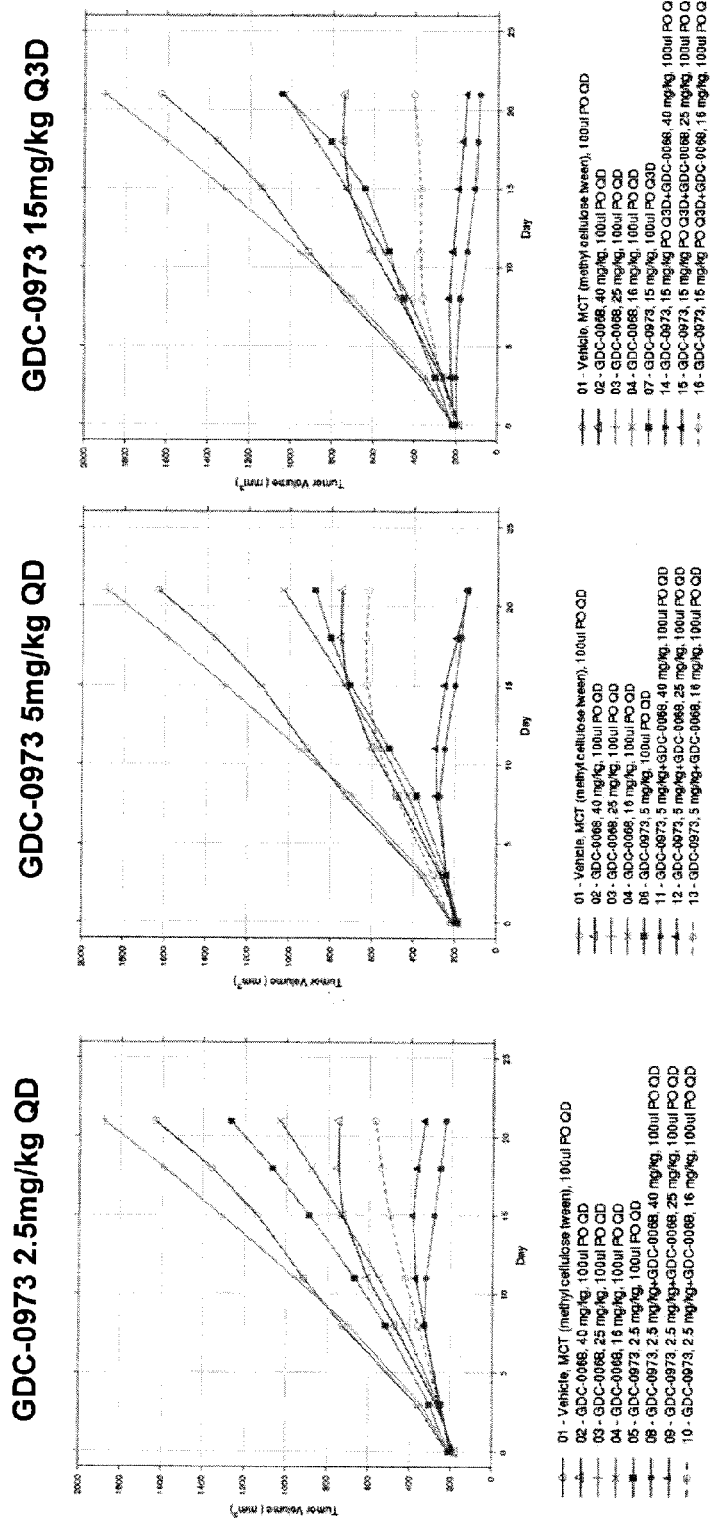
FIG 19 GDC-0068 Dosed PO + GDC-0973 (MEK inhibitor) in 537Mel Melanoma Tumors

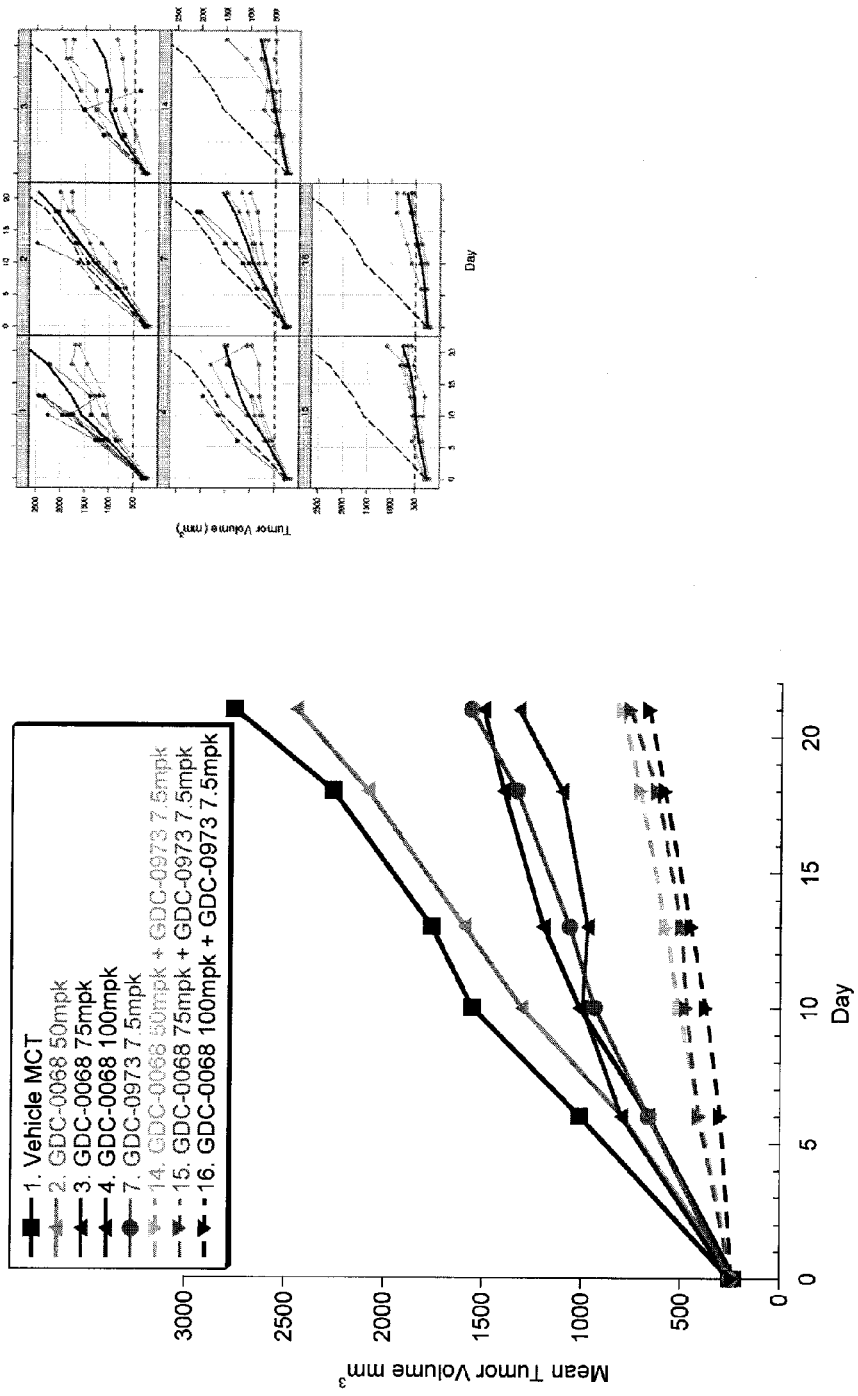
FIG 20 GDC-0068 Dosed PO + GDC-0973 (MEK inhibitor) in A2058 Melanoma Tumors

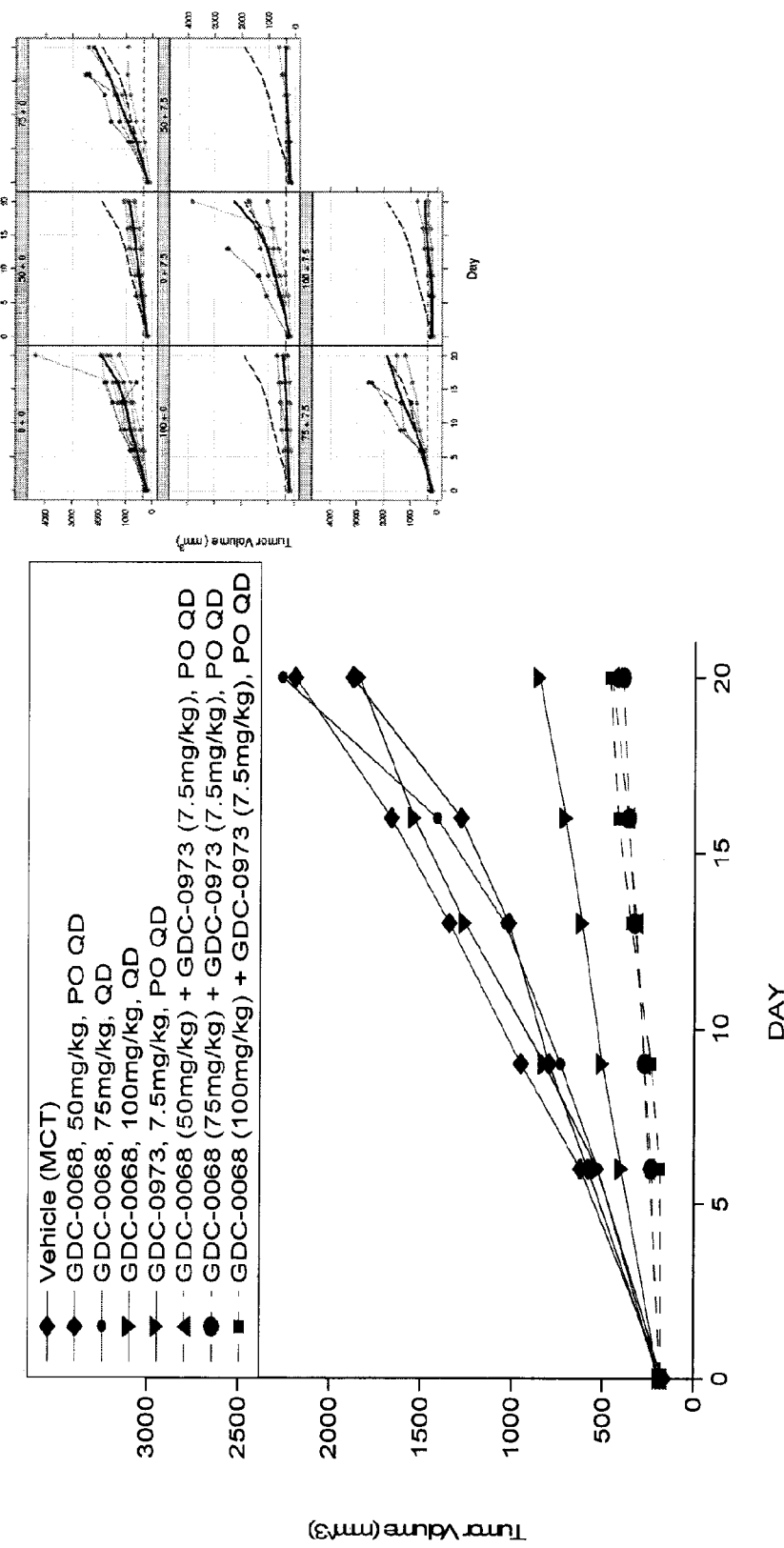
FIG 21 GDC-0068 Dosed PO + GDC-0973 (MEK inhibitor) in HCT-116 Colorectal Tumors

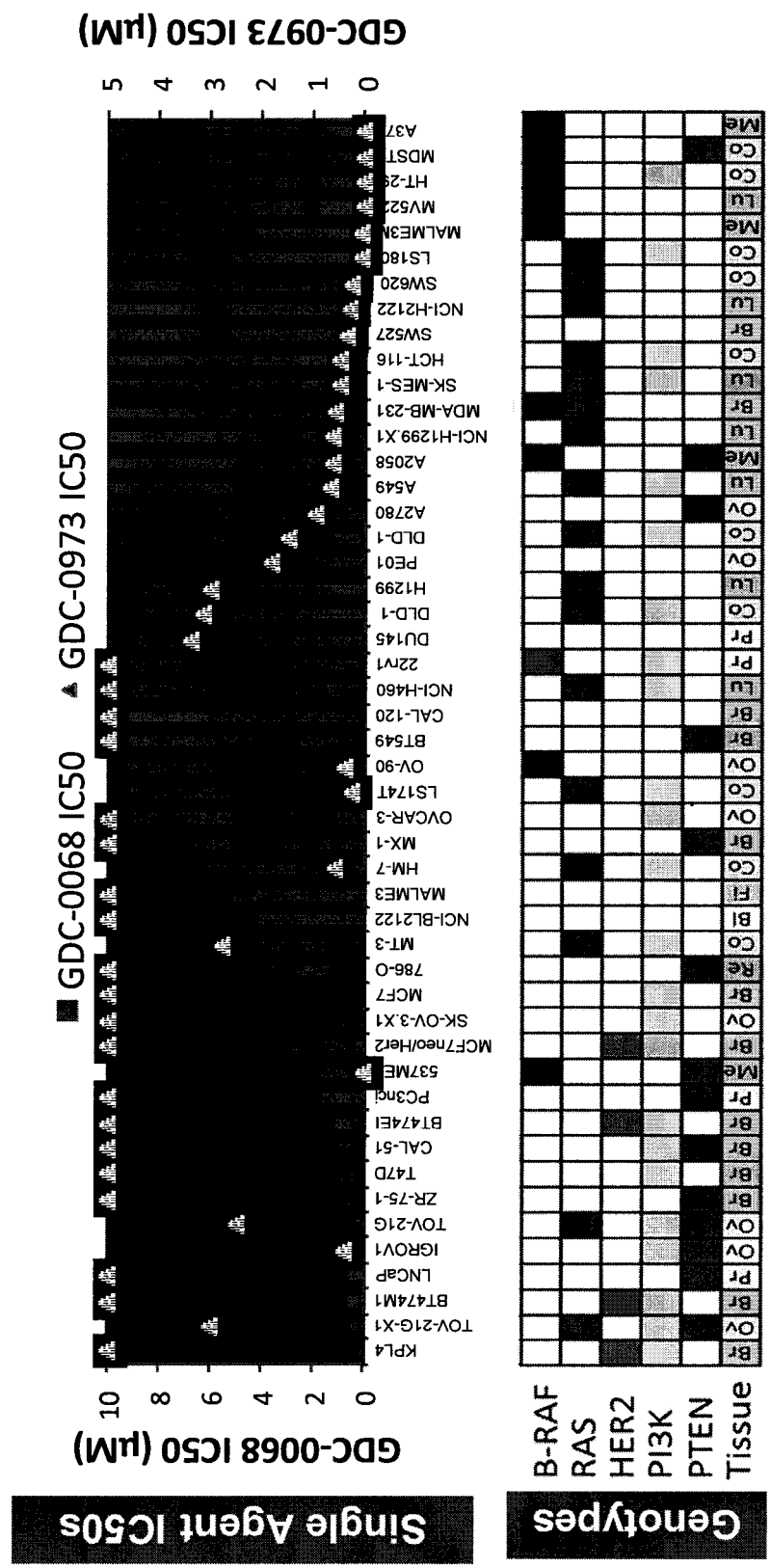
FIG 22a GDC-0068 and GDC-0973 Combination Synergy in Multiple Cell Lines

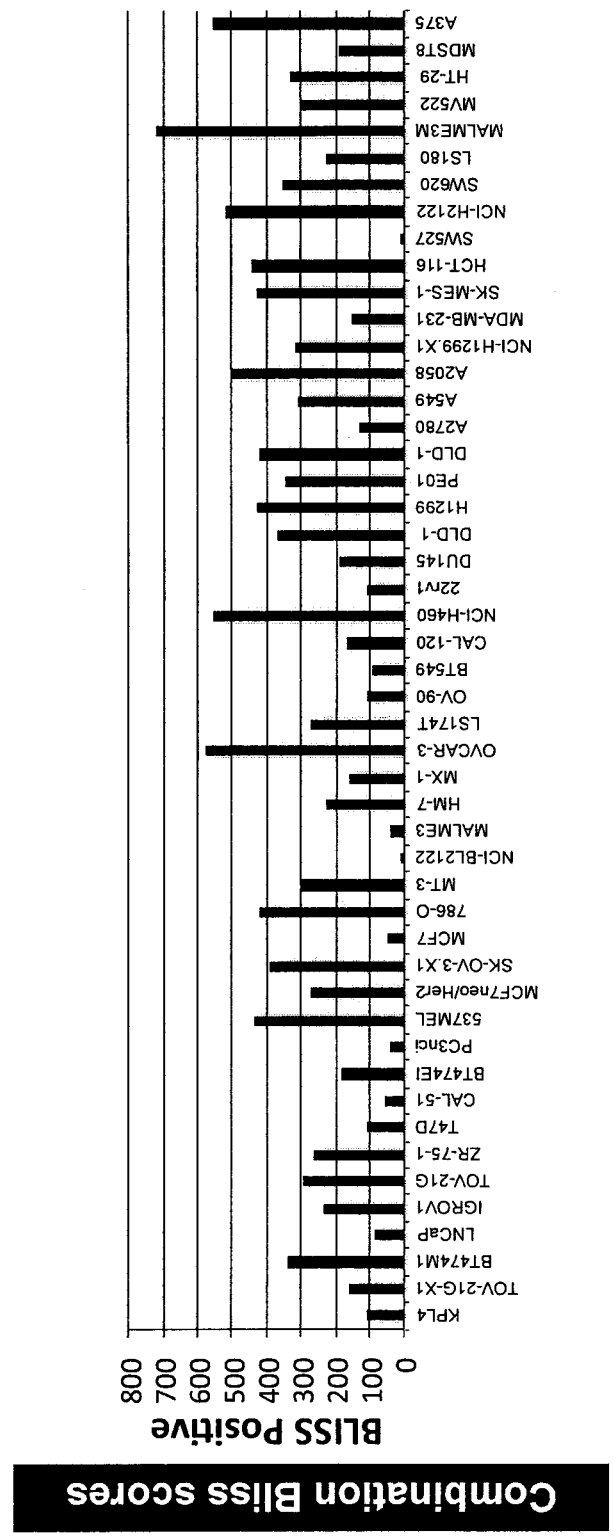
FIG 22b  GDC-0068 and GDC-0973 Combination Synergy in Multiple Cell Lines

COMBINATIONS OF AKT AND MEK INHIBITOR COMPOUNDS, AND METHODS OF USE

PRIORITY OF INVENTION

This application claims priority to U.S. Provisional Application No. 61/471,038 that was filed on Apr. 1, 2011. The entire content of this provisional application is hereby incorporated herein by reference.

FIELD OF THE INVENTION

The invention relates generally to pharmaceutical combinations of compounds with activity against hyperproliferative disorders such as cancer and which include compounds that inhibit AKT kinase activity. The invention also relates to methods of using the combinations for in vitro, in situ, and in vivo diagnosis or treatment of mammalian cells, or associated pathological conditions.

BACKGROUND OF THE INVENTION

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity (Hardie, G. and Hanks, S. (1995) *The Protein Kinase Facts Book. I and II*, Academic Press, San Diego, Calif.). Furthermore, abnormal PK activity has been related to a host of disorders, ranging from relatively non-life threatening diseases such as psoriasis to extremely virulent diseases such as glioblastoma (brain cancer). Protein kinases are an important target class for therapeutic modulation (Cohen, P. (2002) Nature Rev. Drug Discovery 1:309).

International Patent Application Publication Number WO 2008/006040 discusses a number of inhibitors of AKT, including the compound (S)-2-(4-chlorophenyl)-1-(4-((5R, 7R)-7-hydroxy-5-methyl-6,7-dihydro-5H-cyclopenta[d]pyrimidin-4-yl)piperazin-1-yl)-3-(isopropylamino)propan-1-one (formula I):

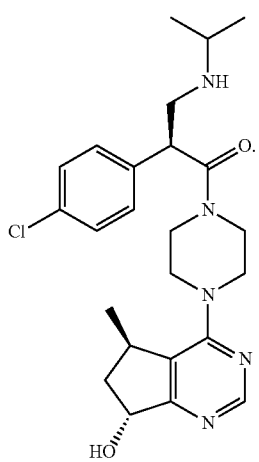

(I)

Currently, there remains a need for improved methods and compositions that can be used to treat hyperproliferative diseases such as cancer.

SUMMARY OF THE INVENTION

It has been determined that additive or synergistic effects in inhibiting the growth of cancer cells in vitro and in vivo can be achieved by administering the compound of formula I or a pharmaceutically acceptable salt thereof in combination with certain other specific agents. The combinations and methods may be useful in the treatment of hyperproliferative disorders such as cancer.

Accordingly, certain embodiments of the invention provide methods for treating a hyperproliferative disorder in a mammal, comprising administering to the mammal a combination of a compound of formula I:

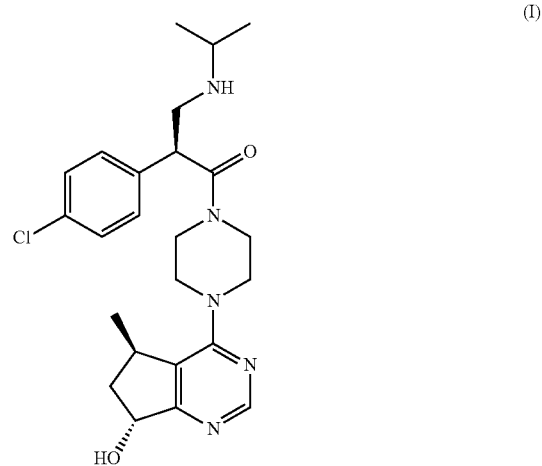 [SMILES: CC(C)NC[C@@H](C(=O)N1CCN(c2ncnc3c2[C@H](C)C[C@H]3O)CC1)c1ccc(Cl)cc1]

(I)

or a pharmaceutically acceptable salt thereof; and another agent selected from GDC-0973, PD-0325901, or a pharmaceutically acceptable salt thereof.

In certain embodiments, the hyperproliferative disorder is cancer.

In certain embodiments, the cancer is associated with PTEN mutation.

In certain embodiments, the cancer is associated with AKT mutation, overexpression or amplification.

In certain embodiments, the cancer is associated with PI3K mutation.

In certain embodiments, the cancer is associated with Her2/ErbB2 amplification

In certain embodiments, the cancer is selected from, mesothelioma, endometrial, pancreatic, breast, lung, ovarian, prostate, melanoma, gastric, colon, renal, head and neck, and giloma.

In certain embodiments, a compound of formula I, or a pharmaceutically acceptable salt thereof, is administered in combination with GDC-0973 or a pharmaceutically acceptable salt thereof.

In certain embodiments, a compound of formula I, or a pharmaceutically acceptable salt thereof, is administered in combination with PD-0325901 or a pharmaceutically acceptable salt thereof.

In certain embodiments, the compound of formula I or the salt thereof is administered simultaneously with the one or more agents.

In certain embodiments, the compound of formula I or the salt and the one or more agents are administered sequentially.

In certain embodiments, administration of the one or more agents begins about 1 to about 10 days before administration of the combination.

In certain embodiments, administration of the compound of formula I or the salt thereof begins about 1 to about 10 days before administration of the combination.

In certain embodiments, administration of the compound of formula I or the salt thereof and administration of the one or more agents begins on the same day.

Certain embodiments of the invention provide a compound of formula I or a pharmaceutically acceptable salt thereof, for therapeutic use for improving the quality of life of a patient treated for a hyperproliferative disorder with an agent selected from GDC-0973 and PD-0325901.

Certain embodiments of the invention provide a method for treating a disease or condition modulated by AKT kinase in a mammal comprising, administering to the mammal, a) a compound of formula I or a pharmaceutically acceptable salt thereof; and b) one or more agents selected from GDC-0973 and PD-0325901.

Certain embodiments of the invention provide a combination of a) a compound of formula I or a pharmaceutically acceptable salt thereof; and b) one or more agents selected from GDC-0973 and PD-0325901 for treating a hyperproliferative disorder.

Certain embodiments of the invention provide a combination of a) a compound of formula I or a pharmaceutically acceptable salt thereof; and b) one or more agents selected from GDC-0973 and PD-0325901 for treating a disease or condition modulated by AKT kinase.

Certain embodiments of the invention provide the use of the combination of a compound of formula I or a pharmaceutically acceptable salt thereof and GDC-0973 and PD-0325901 in the preparation of a medicament for the treatment of a hyperproliferative disorder in a mammal.

Certain embodiments of the invention provide the use of the combination of a compound of formula I or a pharmaceutically acceptable salt thereof and GDC-0973 and PD-0325901 in preparation of a medicament for the treatment of a disease or condition modulated by AKT kinase in a mammal.

Certain embodiments of the invention provide a kit comprising a compound of formula I or a pharmaceutically acceptable salt thereof, a container, and a package insert or label indicating the administration of the compound of formula I with one or more agents selected from GDC-0973 and PD-0325901 for treating a hyperproliferative disorder.

Certain embodiments of the invention provide a product comprising a compound having formula I or a pharmaceutically acceptable salt thereof, and one or more agents selected from GDC-0973 and PD-0325901; as a combined preparation for separate, simultaneous or sequential use in the treatment of a hyperproliferative disorder.

Synergy/additivity is seen when the combination of GDC-0068 and GDC-0973 is dosed in many cell types including melanoma, lung, colon, ovarian, renal, breast, prostate, pancreatic cancer cell lines in vitro, and these finding have been confirmed in melanoma, colon and lung xenograft models in vivo. Synergy is seen in tumor types driven by Ras/Raf or both pathway activations. Melanoma, lung (e.g., NSCLC) and colon lines show synergy when the combination of GDC-0068 and GDC-0973 is dosed in a variety of cells. Breast cancer cells (including luminal (ER+), Her2+, and basal triple negative breast cancers) can also demonstrate synergy when the combination of GDC-0068 and GDC-0973 is dosed. Synergy is observed even in cells sensitive to Meki alone when the combination of GDC-0068 and GDC-0973 is dosed.

It has been discovered that the mutation status of the cancer cell is a biomarker of how the cancer cell will respond to different treatment protocols. For example, cancer cells that have PI3K pathway (e.g. PI3K or AKT) mutations in combination with Kras and/or Braf mutations can display positive (e.g., synergistic) responses to the combination treatments described herein. Further, the PTEN status of the cancer cell is also a biomarker. Accordingly, certain embodiments of the invention include methods of treating cancer cells (in vitro or in vivo) that have combinations of these biomarkers with these combination treatments. Certain embodiments of the invention include selecting patients for combination treatment that have combinations of these biomarkers.

Strong synergy is seen with the combination of GDC-0068 and GDC-0973 in the A2058 (PTEN null/Braf mutant) melanoma model. Comparable single agent tumor growth inhibition (TGI) is seen with all doses of GDC-0973 and higher doses of GDC-0068 (75 and 100 mg/kg). No TGI is seen with 50 mg/kg of GDC-0068. Combination of both drugs were well tolerated in this model, with a maximum weight loss ~13%.

In addition to providing improved treatment for a given hyperproliferative disorder, administration of certain combinations of the invention may improve the quality of life for a patient compared to the quality of life experienced by the same patient receiving a different treatment. For example, administration of a combination of a compound of formula I or a pharmaceutically acceptable salt thereof, and an agent as described herein to a patient may provide an improved quality of life compared to the quality of life the same patient would experience if they received only the chemotherapeutic agent as therapy. For example, the combined therapy with the combination described herein may lower the dose of therapeutic agents needed, thereby lessening the side-effects associated with high-dose chemotherapeutic agents (e.g. nausea, vomiting, hair loss, rash, decreased appetite, weight loss, etc.). The combination may also cause reduced tumor burden and the associated adverse events, such as pain, organ dysfunction, weight loss, etc. Accordingly, one aspect of the invention provides a compound of formula I or a pharmaceutically acceptable salt thereof, for therapeutic use for improving the quality of life of a patient treated for a hyperproliferative disorder with an agent described herein.

BRIEF DESCRIPTION OF THE DRAWINGS

FIG. 1 illustrates results of the combination of GDC-0068 and GDC-0973 (2.5 mg/kg) on tumor volumes.

FIG. 2 illustrates results of the combination of GDC-0068 and GDC-0973 (5.0 mg/kg) on tumor volumes.

FIG. 3 illustrates results of the combination of GDC-0068 and GDC-0973 (7.5 mg/kg) on tumor volumes.

FIG. 4 illustrates results of the combination of GDC-0068 and GDC-0973 against colorectal cancer cell lines in vitro.

FIG. 5 illustrates results of the combination of GDC-0068 and GDC-0973 against HCT-116 (Colon—PI3K and Kras Mutant). Two-dimensional (2D) heatmaps showing the combination effects on cell viability in HCT-116 cells are shown. Increasing concentrations of GDC-0068 are shown on the x-axis and increasing concentrations of GDC-0973 are indicated on the y-axis. Percentage inhibition (% inhibition)

Figure 23:
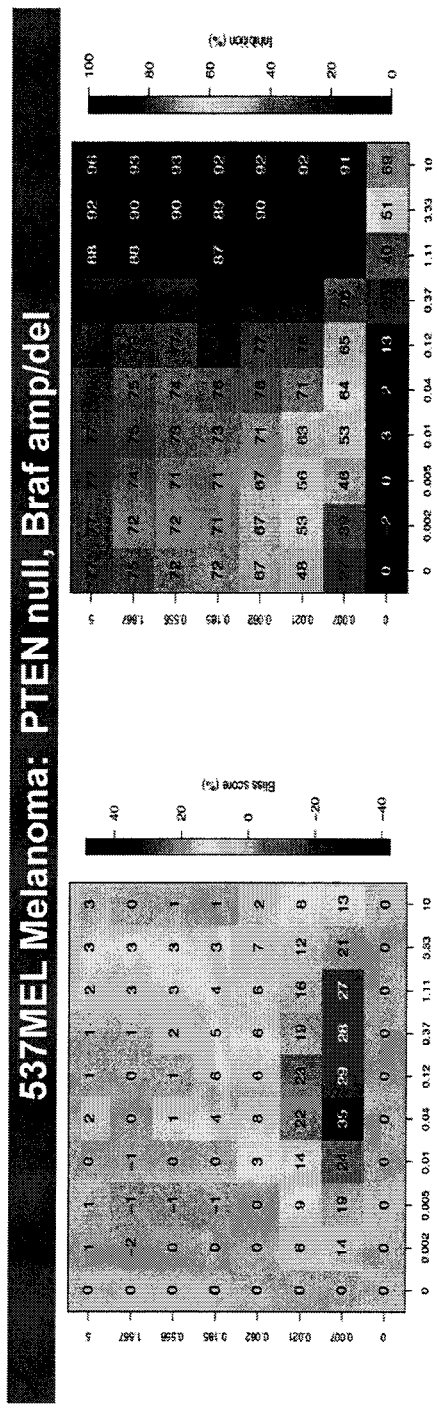

heatmaps are shown on the right indicating the percentage of inhibition at each concentration of GDC-0068 and GDC-0973 either in combination or as single agents; control exposed to the vehicle (DMSO) is set to 0. BLISS scores are calculated for each dose pair and heatmaps shown on the left.

FIG. 6 illustrates results of the combination of GDC-0068 and GDC-0973 against NSCLC cell lines in vitro.

FIG. 7 illustrates results of the combination of GDC-0068 and GDC-0973 against H2122 (NSCLC—Kras Mutant). Two-dimensional (2D) heatmaps showing the combination effects on cell viability in NCI-H2122 cells. Increasing concentrations of GDC-0068 are shown on the x-axis and increasing concentrations of GDC-0973 are indicated on the y-axis. Percentage inhibition (% inhibition) heatmaps are shown on the right indicating the percentage of inhibition at each concentration of GDC-0068 and GDC-0973 either in combination or as single agents; control exposed to the vehicle (DMSO) is set to 0. BLISS scores are calculated for each dose pair and heatmaps shown on the left.

FIG. 8 illustrates results of the combination of GDC-0068 and GDC-0973 against Melanoma cell lines in vitro.

FIG. 9 illustrates results of single agent and the combination of GDC-0068 and GDC-0973 against A2058 (Melonoma—PTEN −/− and Braf Mutant). Two-dimensional (2D) heatmaps showing the combination effects on cell viability in A2058 cells are shown. BLISS scores are calculated for each dose pair and heatmaps shown on the left. Increasing concentrations of GDC-0068 are shown on the x-axis and increasing concentrations of GDC-0973 are indicated on the y-axis. Percentage inhibition (% inhibition) heatmaps are shown on the right indicating the percentage of inhibition at each concentration of GDC-0068 and GDC-0973 either in combination or as single agents; control exposed to the vehicle (DMSO) is set to 0.

FIG. 10 illustrates enhanced knockdown of AKT and MEK pathway activities compared to single agents.

FIG. 11 illustrates results of the combination of GDC-0973 and GDC-0068 against MDA-MB-468 breast cancer cell line.

FIG. 12 results of the combination of GDC-0068 and GDC-0973 against breast cancer cell lines in vitro.

FIG. 13 illustrates results of the combination of GDC-0068 and GDC-0973 against ovarian cancer.

FIG. 14 illustrates results of the combination of GDC-0068 and GDC-0973 against prostate cancer cell lines in vitro.

FIG. 15 illustrates results of the combination of GDC-0068 Dosed PO+GDC-0973 (MEK inhibitor) in MX-1 Breast Tumors.

FIG. 16 illustrates results of the combination of GDC-0068 Dosed PO+GDC-0973 (MEK inhibitor) in H2122 NSCLC Tumors.

FIG. 17 illustrates results of the combination of GDC-0068 Dosed PO+GDC-0973 (MEK inhibitor) in SW1990 Pancreatic Tumors.

FIG. 18 illustrates results of the combination of GDC-0068 Dosed PO+GDC-0973 (MEK inhibitor) in Pa_Tu-8902 Pancreatic Tumors.

FIG. 19 illustrates results of the combination of GDC-0068 Dosed PO+GDC-0973 (MEK inhibitor) in 537Mel Melanoma Tumors.

FIG. 20 illustrates results of the combination of GDC-0068 Dosed PO+GDC-0973 (MEK inhibitor) in A2058 Melanoma Tumors FIG. 21 illustrates results of the combination of GDC-0068 Dosed PO+GDC-0973 (MEK inhibitor) in HCT-116 Colorectal Tumors FIGS. 22a-22b show results of inhibition of cell viability of various cell lines comparing single agent and combination therapies. GDC-0068 cell potency correlated with Akt activation resulting from alterations in PI3K/PTEN/HER2, while GDC-0973 cell potency correlated with MEK activation resulting from RAS or B-RAF mutations. GDC-0068- and GDC-0973-sensitive cell lines are often mutually exclusive. About a third of the cell lines tested showed resistance to both agents (see FIG. 22a-22b). Combination of GDC-0068 and GDC-0973 resulted in enhanced inhibition of cell viability compared with either single agent alone in the majority of cell lines tested. Combination effects were evaluated using the BLISS independence model (Lehár et al. 2007).

FIG. 22a top graph illustrates Single Agent IC50s for GDC-0068 and GDC-0973 in Multiple Cancer Cell Lines. Cells were treated with either GDC-0068 or GDC-0973 or in combination in RPMI+10% FBS at increasing concentrations and assayed after 4 days for viability using CelTiter-Glo. The corresponding bottom graph illustrates GDC-0068 and GDC-0973 combination synergy for the several specific genotypes. Colored Blocking Indicates a Mutation, Deletion, or Activation. Mutations/alterations in B-RAF, RAS, HER2, PI3K or PTEN are indicated by a colored square under each cell line (B-RAF, brown; RAS, red; HER2, blue; PTEN, dark green; for PI3K, light green indicates kinase domain mutations in PIK3CA, light blue indicates non-kinase domain mutations or amplifications). PTEN alterations indicate either a non-detectable signal for this protein by Western blot or a mutation in the gene. Tissue origins for each cell line are also indicated in different colors with letters indicating breast (Br), colon (Co), non small cell lung cancer (Lu), melanoma (Me), ovarian (Ov), prostate (Pr), and renal (Re).

FIG. 22b illustrates total positive combination Bliss Scores for GDC-0068 and GDC-0973 in Multiple Cell Lines. Synergistic effects were observed in multiple cell lines as indicated by the total positive BLISS scores, especially in cell lines with activation of the RAS/RAF pathway or in cell lines with both PI3K/Akt and RAS/RAF pathway activations.

Total positive BLISS scores calculated from the combination of GDC-0068 and GDC-0973 in each cell line.

FIG. 23 illustrates Bliss Heat Map and % Inhibition for GDC-0068 and GDC-0973 in 537MEL Melanoma, PTEN null, Braf amp/del; the Combination of GDC-0068 and GDC-0973 inhibits both pathways and increases cell death.

Figure 24:
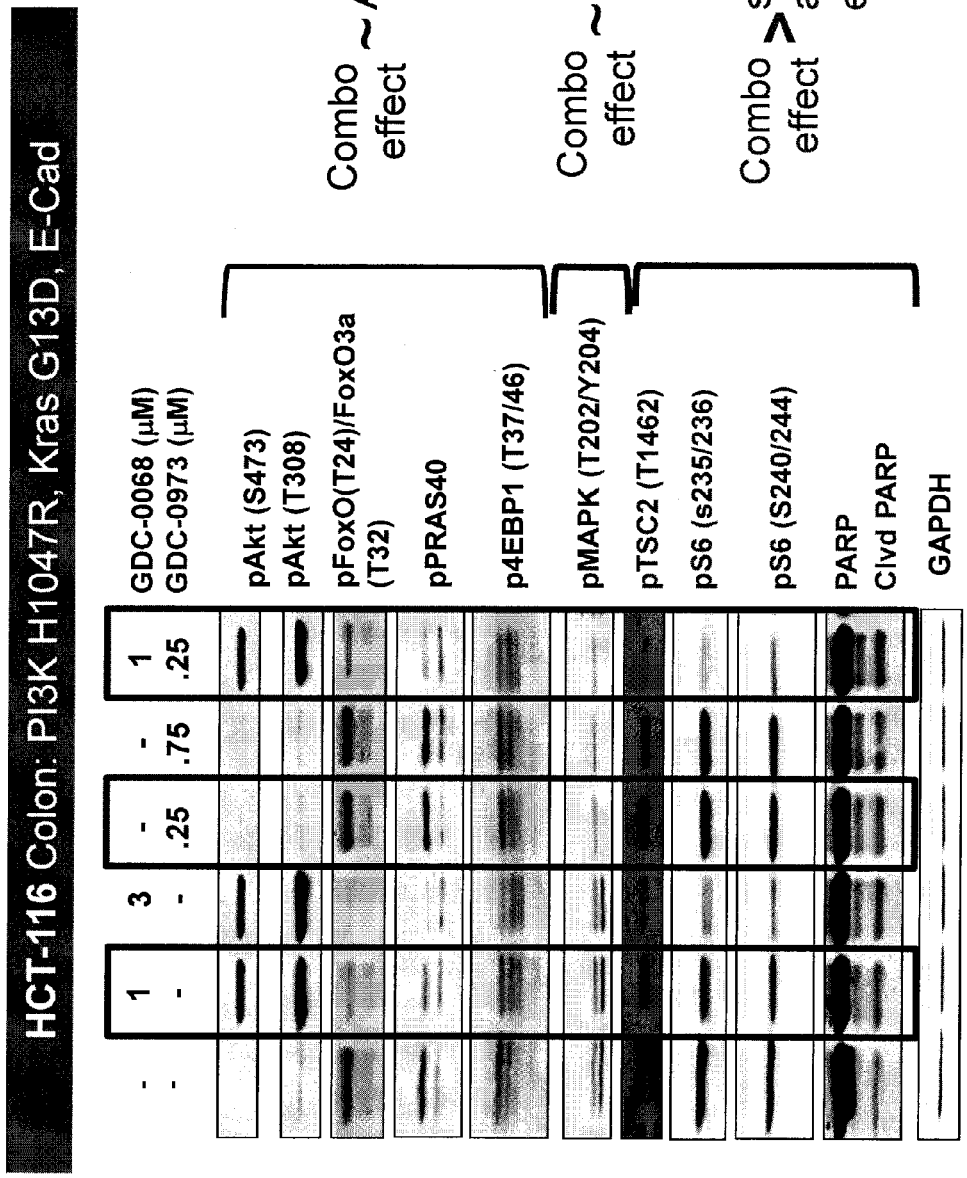

FIG. 24 illustrates Western Blot Analysis for Human HTC 116 Colon Cell Line Treated with GDC-0068 and GDC-0973 for 24 Hours. HCT-116 cells were incubated with GDC-0068 and GDC-0973 at the specified concentrations for about 3 hours. Phosphorylation of Akt, MEK, and their downstream markers were analyzed by Western blots.

Figure 25:
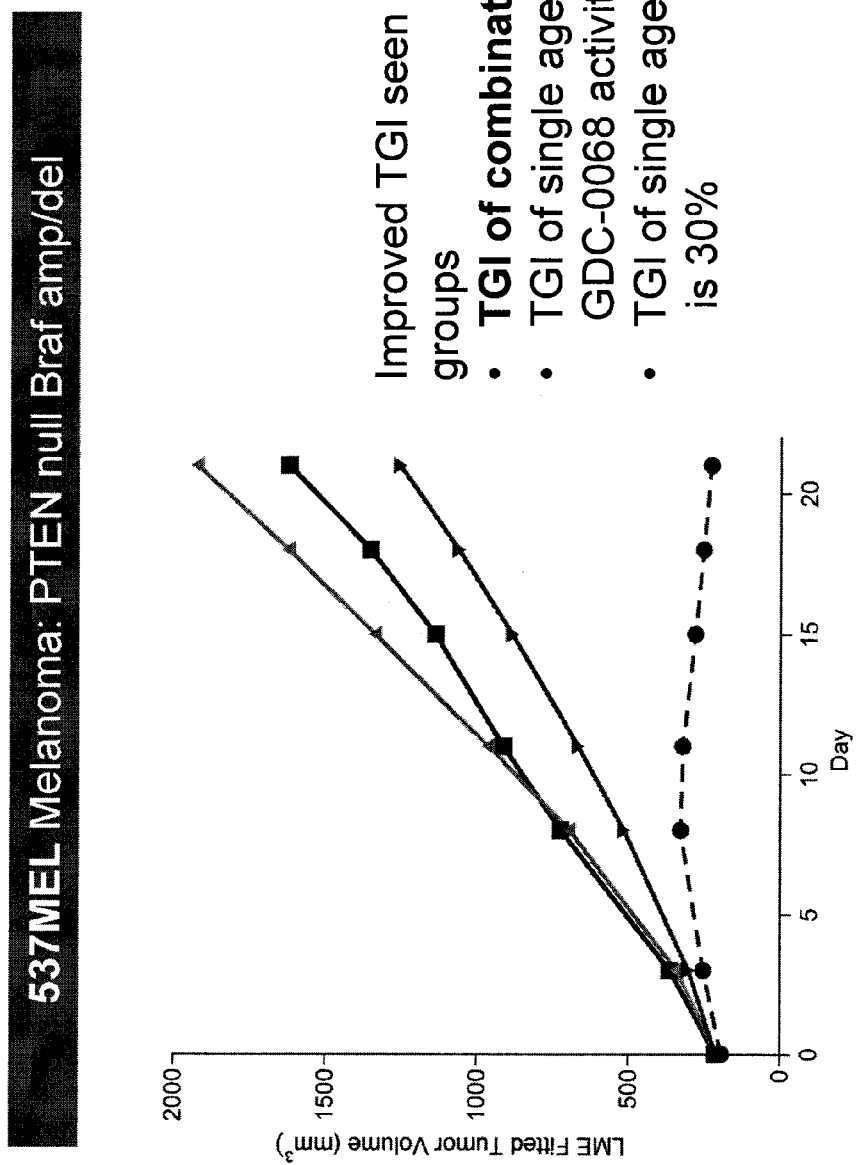

FIG. 25 illustrates the GDC-0068 and GDC-0973 Combination increases efficacy in 537MEL Melanoma, PTEN null, Braf amp/del.

Figure 26:
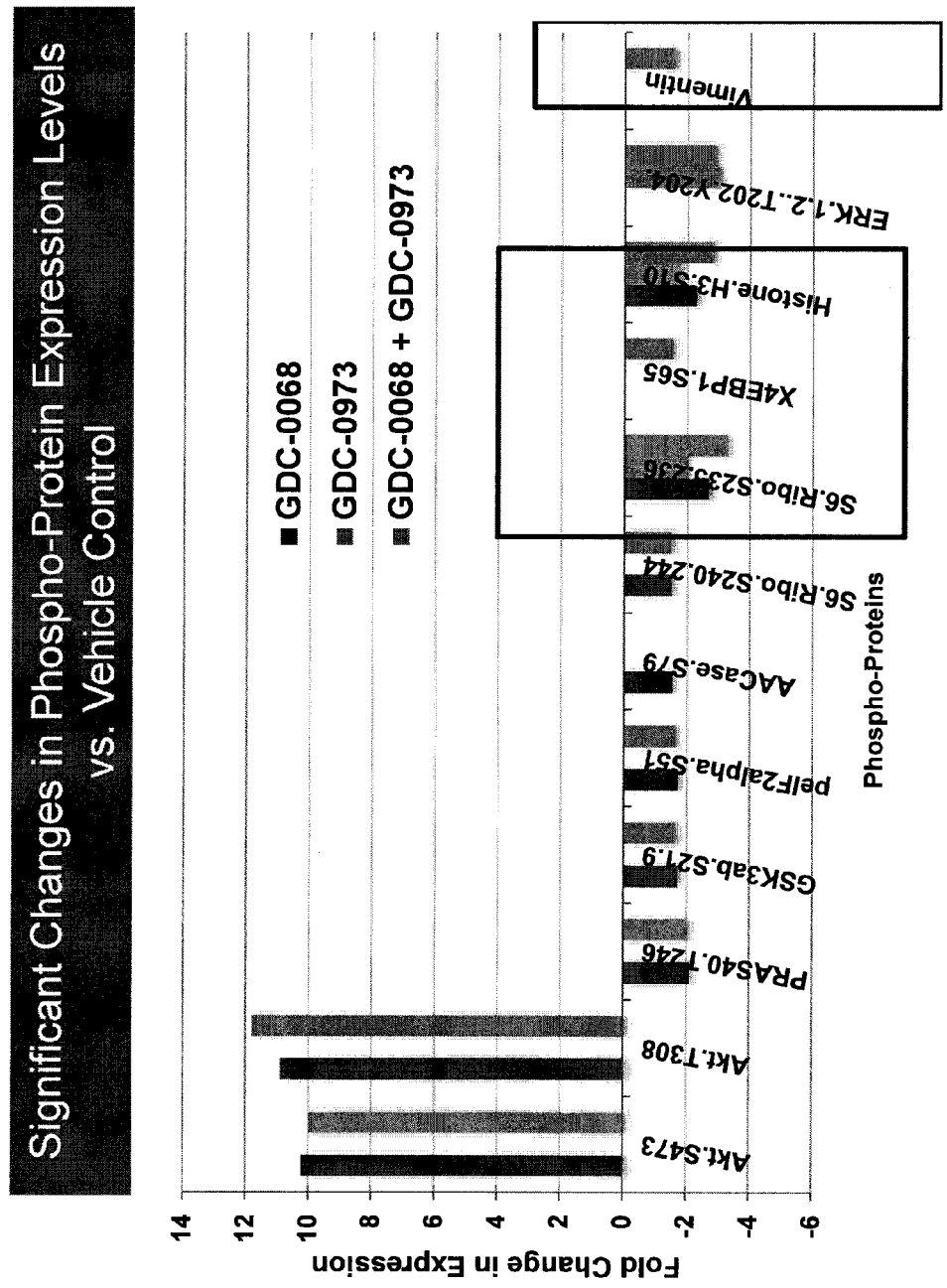

FIG. 26 illustrates significant Changes in the Phospho-Protein Expression Levels vs. Vehicle Control for the GDC-0068 and GDC-0973 Combination. A2058x1 tumors were collected 3 hours after mice were dosed with a single dose of either GDC-0068 at 100 mg/kg or GDC-0973 at 7.5 mg/kg, or the combination. Tumors were analyzed using reverse phase protein array (RPPA).

Figure 27:
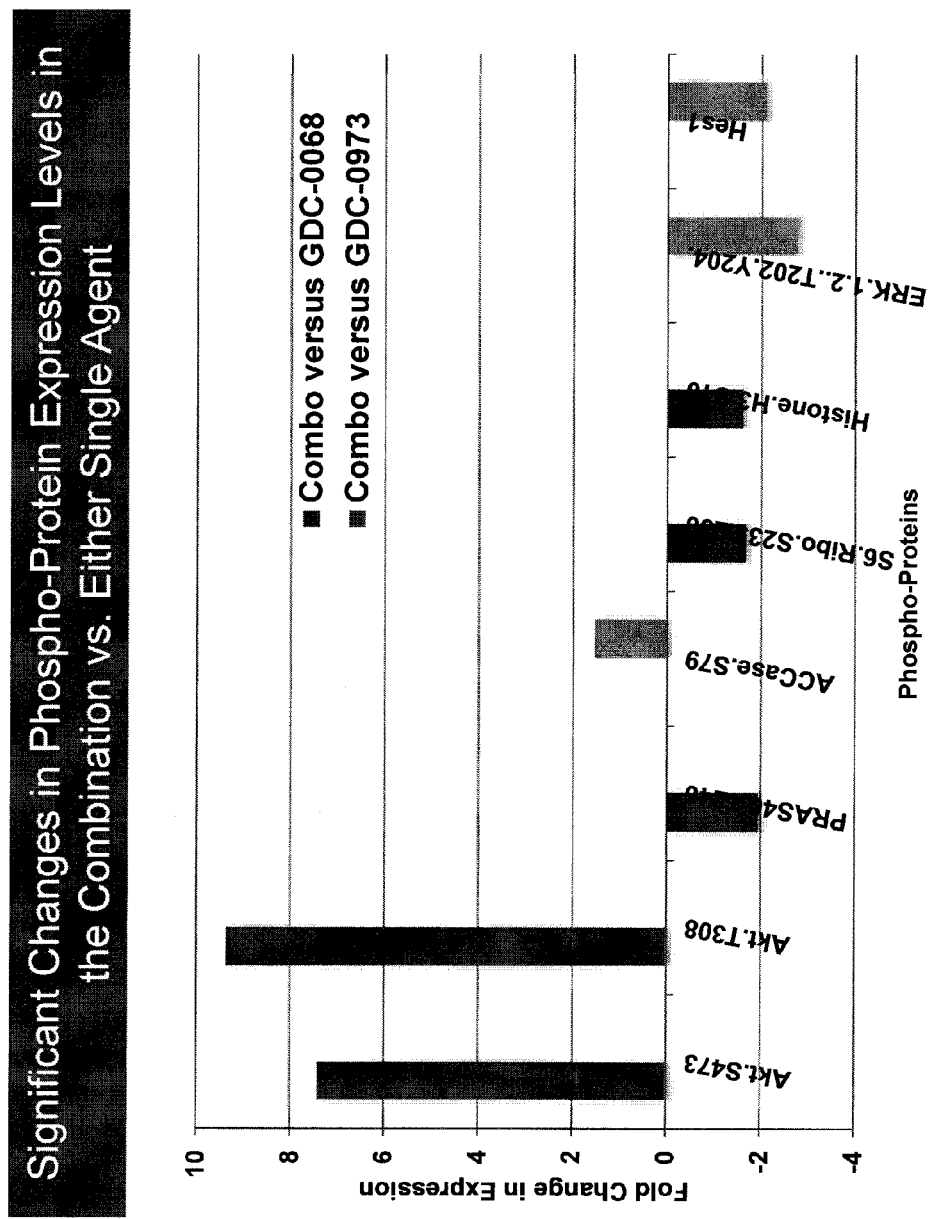

FIG. 27 illustrates significant Changes in the Phospho-Protein Expression Levels for the GDC-0068 and GDC-0973 Combination vs. Either Single Agent in A2058 xenograft tumors post-dosing.

Figure 28:
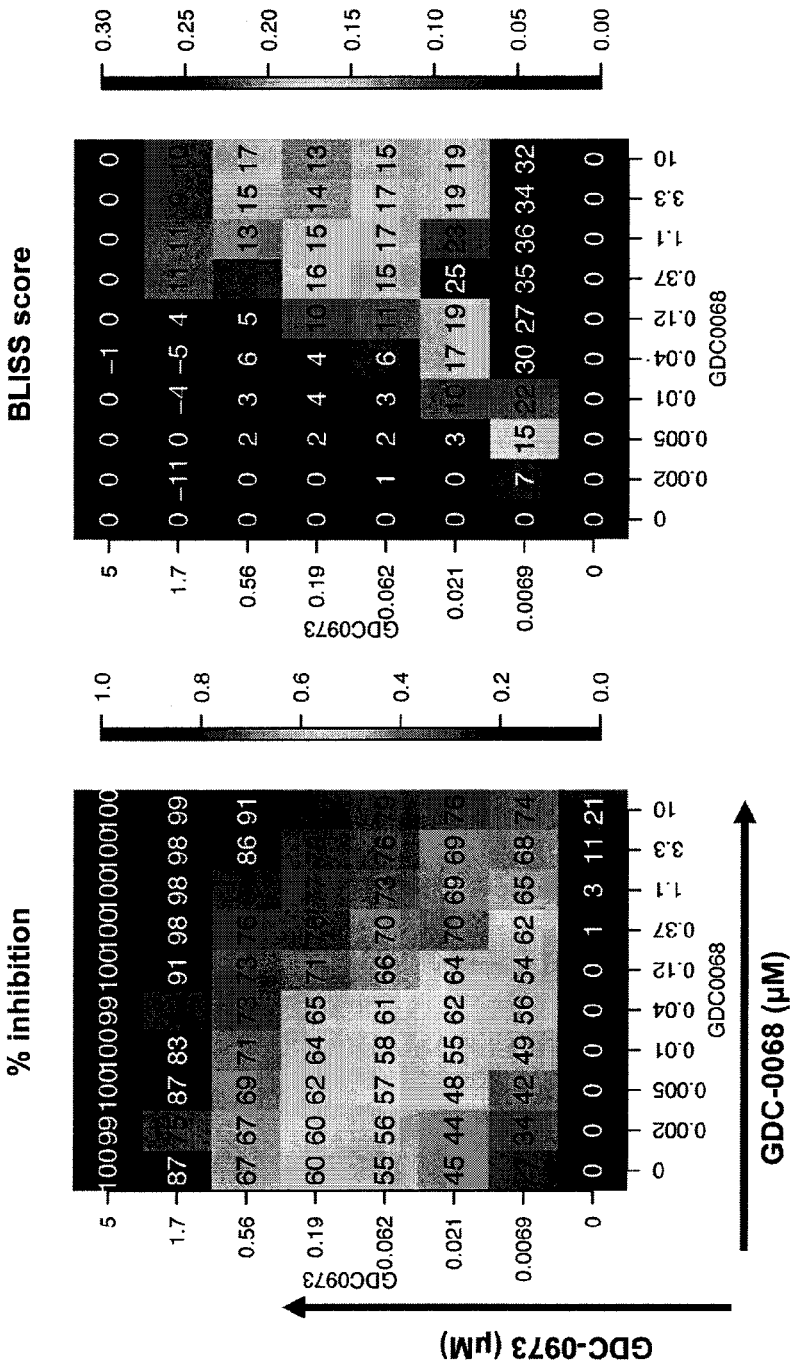

FIG. 28 illustrates two-dimensional (2D) heatmaps showing the combination effects on cell viability in MALME3M cells. Increasing concentrations of GDC-0068 are shown on the x-axis and increasing concentrations of GDC-0973 are indicated on the y-axis. Percentage inhibition (% inhibition) heatmap shows the % inhibition at each concentration of GDC-0068 and GDC-0973 either in combination or as single agents; control was exposed to vehicle (DMSO) and is set to 0.

Figure 29:
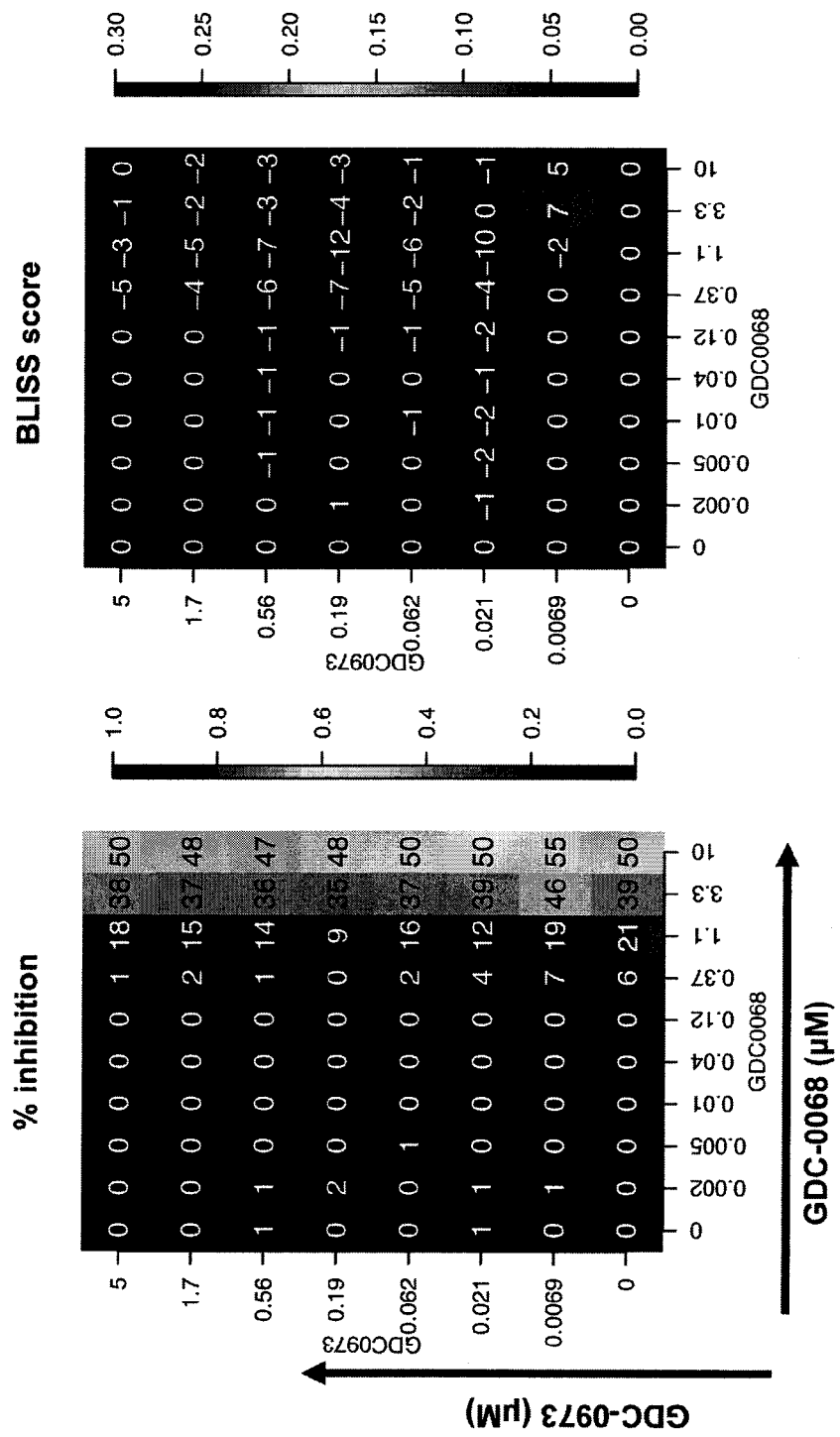

FIG. 29 illustrates two-dimensional (2D) heatmaps showing the combination effects on cell viability in MALME3 cells. Increasing concentrations of GDC-0068 are shown on the x-axis and increasing concentrations of GDC-0973 are indicated on the y-axis. Percentage inhibition (% inhibition) heatmap shows the % inhibition at each concentration of GDC-0068 and GDC-0973 either in combination or as single agents; control was exposed to vehicle (DMSO) and is set to 0. BLISS scores are calculated for each dose pair and heatmaps shown on the right.

Figure 30:
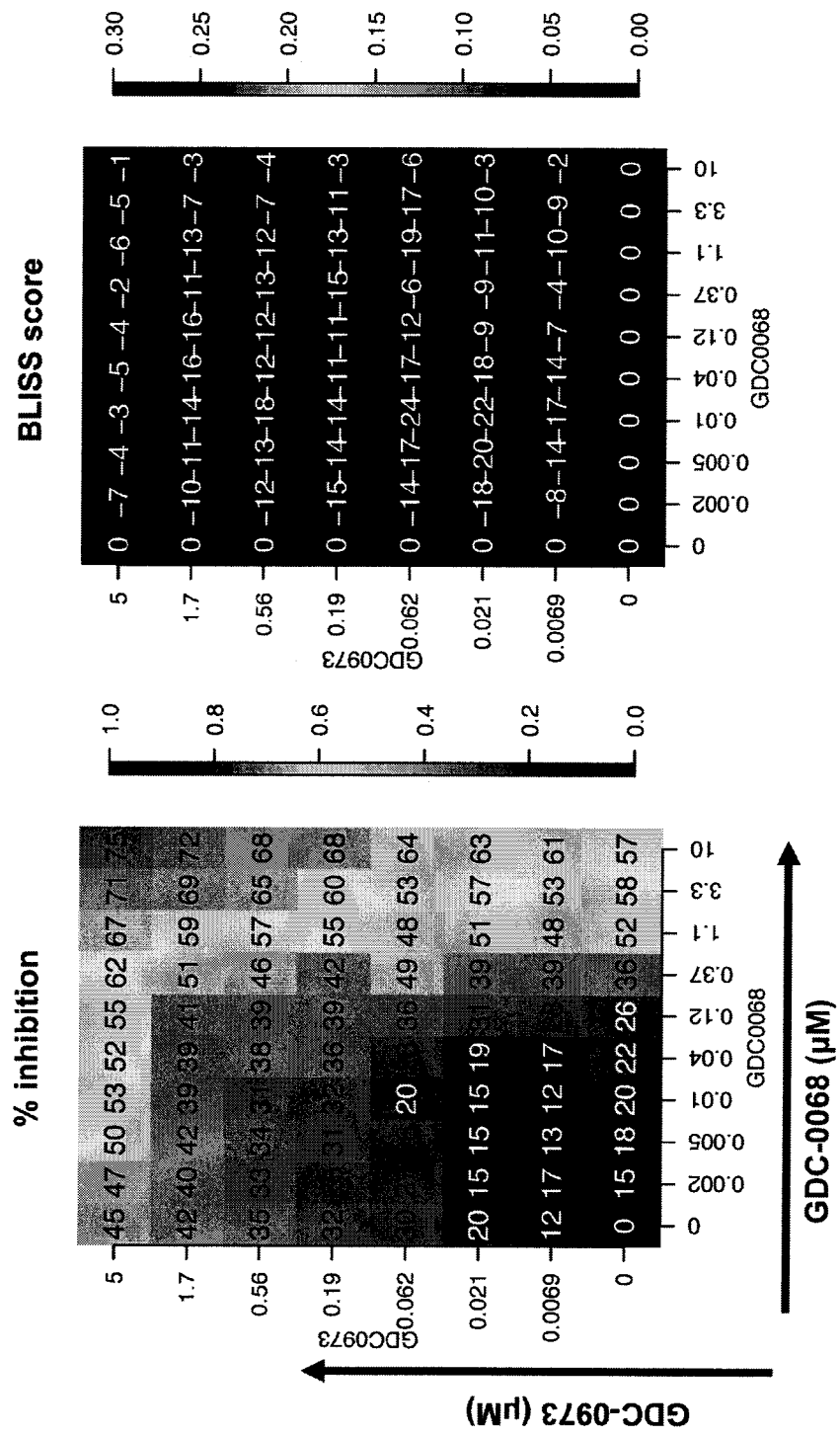

FIG. 30 illustrates two-dimensional (2D) heatmaps showing the combination effects on cell viability in NCI-BL2122 cells. Increasing concentrations of GDC-0068 are shown on the x-axis and increasing concentrations of GDC-0973 are indicated on the y-axis. Percentage inhibition (% inhibition) heatmap shows the % inhibition at each concentration of GDC-0068 and GDC-0973 either in combination or as single agents; control was exposed to vehicle (DMSO) and is set to 0. BLISS scores are calculated for each dose pair and heatmaps shown on the right.

Figure 31:
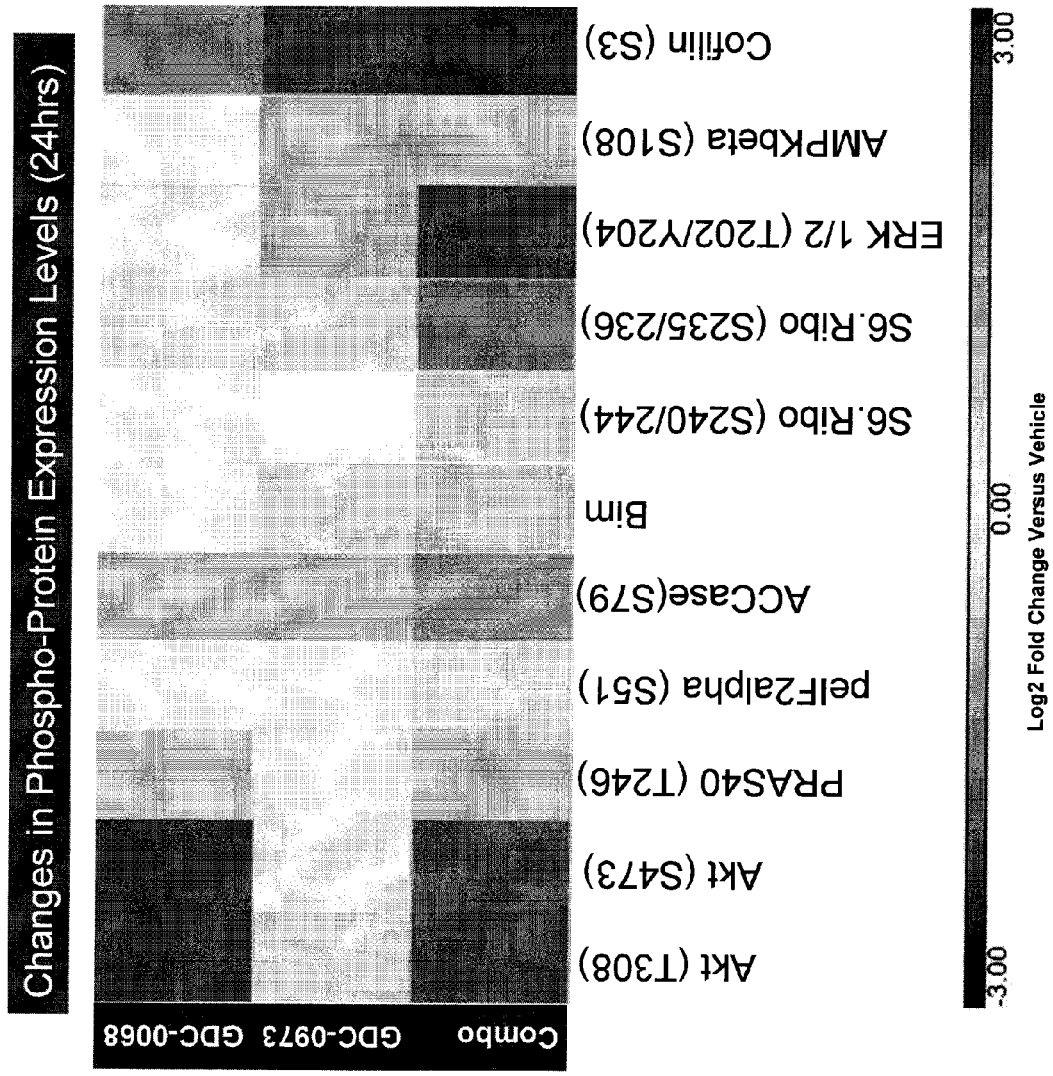

FIG. 31 shows the changes in phospho-protein expression levels (24 hrs) and modulation of the AKT and MEK pathways with the combination of GDC-0068 and GDC-0973. A2058x1 tumors were collected 24 hours after mice were dosed with a single dose of either GDC-0068 at 100 mg/kg or GDC-0973 at 7.5 mg/kg, or the combination. Tumors were analyzed using reverse phase protein array (RPPA).

DETAILED DESCRIPTION OF EXEMPLARY EMBODIMENTS AND DEFINITIONS

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Gastric cancer, as used herein, includes stomach cancer, which can develop in any part of the stomach and may spread throughout the stomach and to other organs; particularly the esophagus, lungs, lymph nodes, and the liver.

A "chemotherapeutic agent" is a biological (large molecule) or chemical (small molecule) compound useful in the treatment of cancer, regardless of mechanism of action.

A "platinum agent" is a chemotherapeutic agent that comprises platinum, for example carboplatin, cisplatin, and oxaliplatin.

The term "mammal" includes, but is not limited to, humans, mice, rats, guinea pigs, monkeys, dogs, cats, horses, cows, pigs, sheep, and poultry. The term patient refers to a mammal, and in one embodiment, the patient is a human.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The desired pharmaceutically acceptable salt may be prepared by any suitable method available in the art. For example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18$^{th}$ ed., (1995) Mack Publishing Co., Easton Pa.; and in The Orange Book (Food & Drug Administration, Washington, D.C. on their website). These disclosures are incorporated herein by reference thereto.

The phrase "pharmaceutically acceptable" indicates that the substance or composition must be compatible chemically and/or toxicologically, with the other ingredients comprising a formulation, and/or the mammal being treated therewith.

The term "synergistic" as used herein refers to a therapeutic combination which is more effective than the additive effects of the two or more single agents. A determination of a synergistic interaction between a compound of formula I or a pharmaceutically acceptable salt thereof and one of GDC-0973 and PD-0325901 may be based on the results obtained from the assays described herein. The results of these assays can be analyzed using the Chou and Talalay combination method and Dose-Effect Analysis with CalcuSyn software in order to obtain a Combination Index (Chou and Talalay, 1984, Adv. Enzyme Regul. 22:27-55). The combinations provided herein have been evaluated in several assay systems, and the data can be analyzed utilizing a standard program for quantifying synergism, additivism, and antagonism among anticancer agents. An example program is that described by Chou and Talalay, in "New Avenues in Developmental Cancer Chemotherapy," Academic Press, 1987, Chapter 2. Combination Index values less than 0.8 indicates synergy, values greater than 1.2 indicate antagonism and values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together. Combination effects were evaluated using both the BLISS independence model and the highest single agent (HSA) model (Lehar et al. 2007, Molecular Systems Biology 3:80). BLISS scores quantify degree of potentiation from single agents and a positive BLISS score (greater than 0) suggests greater than simple additivity. A cumulative positive BLISS score greater than 250 is considered strong synergy observed within the concentration ranges tested. An HSA score (greater than 0) suggests a combination effect greater than the maximum of the single agent responses at corresponding concentrations.

One aspect includes a method of tumor growth inhibition (TGI) in a patient suffering from a cancer comprising a PI3K, AKT or PTEN mutation, and in one example further comprising a RAS/RAF mutation, comprising administering GDC-0068 and one of GDC-0973 and PD-0325901, or a pharmaceutically acceptable salt thereof, to the patient. In certain embodiments, the combination is synergistic. In certain embodiments, the TGI of the combination is greater than the TGI of either GDC-0068 or one of GDC-0973 and PD-0325901 alone. In certain embodiments, the TGI of the combination is about 10, 15, 20, 25, 30, 35, 40, 45, 50, 55, 60, 65, 70 or 75 percent greater than the TGI of either GDC-0068 or one of GDC-0973 and PD-0325901 alone.

Methods of measuring TGI are known in the art. In one example method, average tumor volumes are determined and compared from the patient before and after treatment. Tumor volumes can be measured in two dimensions (length and width) using any method in the art, for example UltraCal IV calipers (Fred V. Fowler Company) or by PET (positron emission tomography), or by some other method. The formula tumor volume $(mm^3)$=(length×width$^2$)×0.5 can be used. Measuring tumor volumes over multiple time periods can be done using a mixed-modeling Linear Mixed Effects (LME) approach (Pinheiro et al. 2009). This approach can address both repeated measurements (and multiple patients). Cubic regression splines can be used to fit a non-linear profile to the time courses of tumor volume at each dose level. These non-linear profiles can then be related to dose within the mixed model. Tumor growth inhibition as a percent of vehicle can be calculated as a percent area under the fitted curve (AUC) per day in relation to the vehicle, using the following formula:

$$\% \ TGI = 100\left[1 - \left(\frac{AUC_{treatment}/\text{day}}{AUC_{vehicle}/\text{day}}\right)\right]$$

Using this formula, a TGI value of 100% indicates tumor stasis, greater than about 1% but less than about 100% indicates tumor growth inhibition, and greater than about 100% indicates tumor regression.

Preparation of a Compound of Formula I

The compound of formula I and salts thereof can be prepared as described in International Patent Application Publication Number WO 2008/006040 or as described in Example 1 below. In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In any of the synthetic methods for preparing compounds of Formula I, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., J. Chromatogr., (1975) 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993). Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (–)menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. of Chromatogr., (1990) 513:375-378). Enriched or purified enantiomers can be distinguished by methods used to distinguish other chiral molecules with asymmetric carbon atoms, such as optical rotation and circular dichroism.

Chemotherapeutic Agents

Certain chemotherapeutic agents have demonstrated surprising and unexpected properties in combination with a compound of formula I or a pharmaceutically acceptable salt thereof in inhibiting cellular proliferation in vitro and in vivo. Such chemotherapeutic agents include GDC-0973 and PD-0325901.

GDC-0973, also known as XL-518, is a selective inhibitor of MEK, also known as mitogen activated protein kinase kinase (MAPKK), which is a key component of the RAS/RAF/MEK/ERK pathway that is frequently activated in human tumors. Inappropriate activation of the MEK/ERK pathway promotes cell growth in the absence of exogenous growth factors. A Phase I clinical trial evaluating GDC-0973 for solid tumors is ongoing. GDC-0973 can be prepared as described in International Patent Application Publication Number WO2007044515(A1). GDC-0973 has the name: (S)-(3,4-difluoro-2-(2-fluoro-4-iodophenylamino)phenyl)(3-hydroxy-3-(piperidin-2-yl)azetidin-1-yl)methanone, and the following structure:

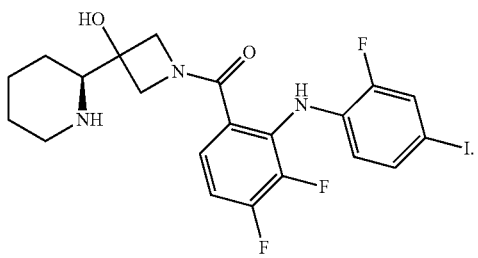 [SMILES: O=C(c1ccc(F)c(F)c1Nc1ccc(I)cc1F)N1CC(O)([C@@H]2CCCCN2)C1]

PD-0325901 (CAS Reg. No. 391210-10-9, Pfizer) is a second-generation, non-ATP competitive, allosteric MEK inhibitor for the potential oral tablet treatment of cancer (U.S. Pat. No. 6,960,614; U.S. Pat. No. 6,972,298; US 2004/147478; US 2005/085550). Phase II clinical trials have been conducted for the potential treatment of breast tumors, colon tumors, and melanoma. PD-0325901 is named as (R)-N-(2,3-dihydroxypropoxy)-3,4-difluoro-2-(2-fluoro-4-iodophenylamino)benzamide, and has the structure:

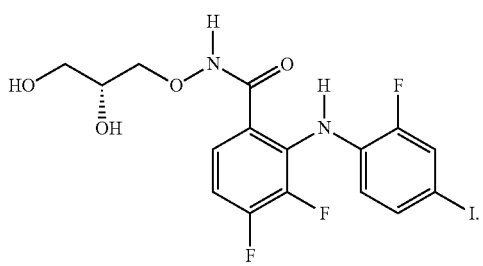 [SMILES: O=C(NOC[C@H](O)CO)c1ccc(F)c(F)c1Nc1ccc(I)cc1F]

Pharmaceutical Compositions

Pharmaceutical compositions or formulations of the present invention include combinations of the compound of formula I or a pharmaceutically acceptable salt thereof, a chemotherapeutic agent, and one or more pharmaceutically acceptable carrier, glidant, diluent, or excipient.

One example includes a first formulation for oral delivery of GDC-0068, or a salt thereof, and one or more pharmaceutically acceptable carrier, glidant, diluent, or excipient, and a second formulation for oral delivery of one of GDC-0973 and PD-0325901, or a salt thereof, and one or more pharmaceutically acceptable carrier, glidant, diluent, or excipient. In one example, the second formulation comprises GDC-0973 or a salt thereof.

The compound of formula I or the a pharmaceutically acceptable salt thereof, and chemotherapeutic agents may exist in unsolvated as well as solvated forms with pharmaceutically acceptable solvents such as water, ethanol, and the like, and it is intended that the invention embrace both solvated and unsolvated forms.

The compound of formula I or a pharmaceutically acceptable salt thereof, and chemotherapeutic agents may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerization. Valence tautomers include interconversions by reorganization of some of the bonding electrons.

Pharmaceutical compositions encompass both the bulk composition and individual dosage units comprised of more than one (e.g., two) pharmaceutically active agents including a compound of formula I or a pharmaceutically acceptable salt thereof and a chemotherapeutic agent described herein, along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the herein-described method of treating a patient by administering a pharmaceutical composition of the present invention is also intended to encompass the administration of the bulk composition and individual dosage units.

Pharmaceutical compositions also embrace isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium ($^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy.

The compound of formula I or a pharmaceutically acceptable salt thereof and chemotherapeutic agents are formulated in accordance with standard pharmaceutical practice for use in a therapeutic combination for therapeutic treatment (including prophylactic treatment) of hyperproliferative disorders in mammals including humans. The invention provides a pharmaceutical composition comprising a compound of formula I or a pharmaceutically acceptable salt thereof and one or more of the chemotherapeutic agents described herein in association with one or more pharmaceutically acceptable carrier, glidant, diluent, or excipient.

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds may be prepared for various routes and types of administration. For example, the compound of formula I or a pharmaceutically acceptable salt thereof having the desired degree of purity may optionally be mixed with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations will be dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa.

Sustained-release preparations of a compound of formula I or a pharmaceutically acceptable salt thereof may be prepared. Suitable examples of sustained-release preparations include semipermeable matrices of solid hydrophobic polymers containing a compound of Formula I or a pharmaceutically acceptable salt thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D (−) 3-hydroxybutyric acid.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences 18$^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of formula I or a pharmaceutically acceptable salt thereof and/or chemotherapeutic agent suitable for oral administration may be prepared as discrete units such as pills, hard or soft e.g., gelatin capsules, cachets, troches, lozenges, aqueous or oil suspensions, dispersible powders or granules, emulsions, syrups or elixirs each containing a predetermined amount of a compound of formula I or a pharmaceutically acceptable salt thereof and/or a chemotherapeutic agent. The amount of compound of Formula I or a pharmaceutically acceptable salt thereof and the amount of chemotherapeutic agent may be formulated in a pill, capsule, solution or suspension as a combined formulation. Alternatively, the compound of formula I or a pharmaceutically acceptable salt thereof and the chemotherapeutic agent may be formulated separately in a pill, capsule, solution or suspension for administration by alternation.

Formulations may be prepared according to any method known to the art for the manufacture of pharmaceutical compositions and such compositions may contain one or more agents including sweetening agents, flavoring agents, coloring agents and preserving agents, in order to provide a palatable preparation. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

The tablets may optionally be coated or scored and optionally are formulated so as to provide slow or controlled release of the active ingredient therefrom. Tablet excipients of a pharmaceutical formulation may include: Filler (or diluent) to increase the bulk volume of the powdered drug making up the tablet; Disintegrants to encourage the tablet to break down into small fragments, ideally individual drug particles, when it is ingested and promote the rapid dissolution and absorption of drug; Binder to ensure that granules and tablets can be formed with the required mechanical strength and hold a tablet together after it has been compressed, preventing it from breaking down into its component powders during packaging, shipping and routine handling; Glidant to improve the flowability of the powder making up the tablet during production; Lubricant to ensure that the tableting powder does not adhere to the equipment used to press the tablet during manufacture. They improve the flow of the powder mixes through the presses and minimize friction and breakage as the finished tablets are ejected from the equipment; Antiadherent with function similar to that of the glidant, reducing adhesion between the powder making up the tablet and the machine that is used to punch out the shape of the tablet during manufacture; Flavor incorporated into tablets to give them a more pleasant taste or to mask an unpleasant one, and Colorant to aid identification and patient compliance.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner, including a mixture of at least one emulsifier with a fat or an oil, or with both a fat and an oil. Preferably, a hydrophilic emulsifier is included together with a lipophilic emulsifier which acts as a stabilizer. Together, the emulsifier(s) with or without stabilizer(s) make up an emulsifying wax, and the wax together with the oil and fat comprise an emulsifying ointment base which forms the oily dispersed phase of cream formulations. Emulsifiers and emulsion stabilizers suitable for use in the formulation include Tween® 60, Span® 80, cetostearyl alcohol, benzyl alcohol, myristyl alcohol, glyceryl monostearate and sodium lauryl sulfate.

Aqueous suspensions of the pharmaceutical formulations contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising a compound of formula I or a pharmaceutically acceptable salt thereof and at least one of the chemotherapeutic agents described herein together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compound of formula I or a pharmaceutically acceptable salt thereof may be employed in combination with other chemotherapeutic agents for the treatment of a hyperproliferative disease or disorder, including tumors, cancers, and neoplastic tissue, along with pre-malignant and non-neoplastic or non-malignant hyperproliferative disorders. In certain embodiments, a compound of Formula I or a pharmaceutically acceptable salt thereof is combined in a dosing regimen as combination therapy, with a second compound that has anti-hyperproliferative properties or that is useful for treating the hyperproliferative disorder. The second compound of the dosing regimen preferably has complementary activities to the compound of formula I or a pharmaceutically acceptable salt thereof, and such that they do not adversely affect each other. Such compounds may be administered in amounts that are effective for the purpose intended. In one embodiment, the therapeutic combination is administered by a dosing regimen wherein the therapeutically effective amount of a compound of formula I, or a pharmaceutically acceptable salt thereof is administered in a range from twice daily to once every three weeks (q3wk), and the therapeutically effective amount of the chemotherapeutic agent is administered in a range from twice daily to once every three weeks.

The combination therapy may be administered as a simultaneous or sequential regimen. When administered sequentially, the combination may be administered in two or more administrations. The combined administration includes coadministration, using separate formulation, and consecutive administration in either order, wherein preferably there is a time period while both (or all) active agents simultaneously exert their biological activities.

In one specific aspect of the invention, the compound of formula I or the pharmaceutically acceptable salt thereof can be administered for a time period of about 1 to about 10 days after administration of the one or more agents begins. In another specific aspect of the invention, the compound of formula I or the pharmaceutically acceptable salt thereof can be administered for a time period of about 1 to 10 days before administration of the combination begins. In another specific aspect of the invention, administration of the compound of formula I or the pharmaceutically acceptable salt thereof and administration of the chemotherapeutic agent begin on the same day.

Suitable dosages for any of the above coadministered agents are those presently used and may be lowered due to the combined action (synergy) of the newly identified agent and other chemotherapeutic agents or treatments, such as to increase the therapeutic index or mitigate toxicity or other side-effects or consequences.

In a particular embodiment of anti-cancer therapy, a compound of formula I, or pharmaceutically acceptable salt thereof, may be combined with a chemotherapeutic agent, as well as combined with surgical therapy and radiotherapy. The amounts of the compound of formula I or a pharmaceutically acceptable salt thereof and the other pharmaceutically active chemotherapeutic agent(s) and the relative timings of administration will be selected in order to achieve the desired combined therapeutic effect.

Administration of Pharmaceutical Compositions

The compounds may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices.

Formulation of drugs is discussed in Remington's Pharmaceutical Sciences, 18$^{th}$ Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, 2$^{nd}$ Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose to treat human patients may range from about 20 mg to about 1600 mg per day of the compound of formula I or a pharmaceutically acceptable salt thereof. A typical dose may be about 50 mg to about 800 mg of the compound. A dose may be administered once a day (QD), twice per day (BID), or more frequently, depending on the pharmacokinetic (PK) and pharmacodynamic (PD) properties, including absorption, distribution, metabolism, and excretion of the particular compound. In addition, toxicity factors may influence the dosage and administration dosing regimen. When administered orally, the pill, capsule, or tablet may be ingested twice daily, daily or less frequently such as weekly or once every two or three weeks for a specified period of time. The regimen may be repeated for a number of cycles of therapy.

Methods of Treatment

Therapeutic combinations of: (1) a compound of formula I or a pharmaceutically acceptable salt thereof, and (2) a chemotherapeutic agent are useful for treating diseases, conditions and/or disorders including, but not limited to, those modulated by AKT kinase in a mammal. Cancers which can be treated according to the methods of this invention include, but are not limited to, mesothelioma, endometrial, glioma, pancreatic, breast, lung, ovarian, prostate, melanoma, gastric, colon, head and neck.

It has been determined that certain combinations of the invention provide improved effects against certain cancer phenotypes. For example, certain combinations of the invention provide improved effects against cancers associated with PTEN mutation (or low or null status), AKT mutation (or high pAKT expression or amplification levels), PI3K mutation, Her2/ErbB2 amplification, RAS mutations, RAF mutations or a combination of the above.

Accordingly, certain combinations described herein may be particularly useful against these types of cancers.

For example, in colorectal cancer, PI3k/AKT mutations (e.g. PI3K H1047R, E545K, D549N, P421L, L568F, L569F, P449T or combinations thereof) in combination with RAS/RAF mutations (KRAS G13D, G12D, G12V or combinations thereof) are predictive of strong responses to the combinations herein and strong synergy was seen for the combination of GDC-0068 plus GDC-0973.

Also, in non-small cell lung cancer, strong synergy was seen for the combination of GDC-0068 plus GDC-0973 where: (i) combinations of PI3k/AKT mutations (PI3k E545K, L997P, M772X, N996H or combinations thereof) and RAS/RAF mutations (Q61H, G12C, Q61K, N85K, G12S, BRAF V600E or combinations thereof) occur, and (ii) combinations of RAS/RAF occur without PI3k mutations.

Also, in melanoma, strong synergy was seen for the combination of GDC-0068 plus GDC-0973 where: (i) BRAF V600E mutations occur, and (ii) BRAF V600E mutations or deletions or amplifications occur with PTEN mutations, null or low status or with high pAKT expression or activity levels.

Kits for testing whether a patient comprises the BRAF V600E mutation are commercially available. One example is the COBAS® 4800 BRAF V600 Mutation Test (Roche Molecular Systems Inc.), which detects the BRAF V600E mutation in formalin-fixed, paraffin-embedded (FFPET) human melanoma tissue. It is approved in the U.S. as a companion diagnostic for treatment with vemurafenib or a pharmaceutically acceptable salt thereof, designed to treat patients whose melanoma tumors harbor the mutated form of the BRAF gene. In pre-clinical and clinical investigations, the Cobas® BRAF Mutation Test had 97.3% positive agreement in detecting the BRAF V600E (1799 T>A) mutation, which represents >~85% of all BRAF mutations reported in the COSMIC database. In formalin-fixed, paraffin-embedded tissue (FFPET), the Cobas® BRAF Mutation Test can detect V600E mutations at >5% mutation level. The test may also detect other V600 mutations such as V600D and V600K. The Cobas® BRAF Mutation Test can be performed in <8 hours from receipt of specimen, such as tissue sample or tumor cells obtained from the patient. The Cobas® 4800 BRAF V600 Mutation Test is a real-time PCR test on the Cobas® 4800 System, v2.0, and is intended to be used as an aid in selecting melanoma patients whose tumors carry the BRAF V600E mutation.

PTEN null (or low) status may be measured by any suitable means as is known in the art. In one example, IHC is used. Alternatively, Western blot analysis can be used. Antibodies to PTEN are commercially available (Cell Signaling Technology, Beverly, Mass., Cascade Biosciences, Winchester, Mass.). Example procedures for IHC and Western blot analysis for PTEN status are described in Neshat, M. S. et al. Enhanced sensitivity of PTEN-deficient tumors to inhibition of FRAP/mTOR, *Proc. Natl. Acad. Sci. USA* 98, 10314-10319 (2001) and Perren, A., et. al. Immunohistochemical Evidence of Loss of PTEN Expression in Primary Ductal Adenocarcinomas of the Breast, *American Journal of Pathology*, Vol. 155, No. 4, October 1999. Additionally, cancers associated with AKT mutation, PI3K mutation, and with Her2/ErbB2 amplification can be identified using techniques that are known in the art.

The level of activation or phosphorylation of AKT ("pAKT") compared to the level of non-activated or non-phosphorylated AKT in a given sample can be measured by methods known in the art. The pAKT status can be expressed in terms of a ratio (e.g. amount of pAKT in a tumor cell divided by amount pAKT in a non-tumorous cell of the same type) or a subtraction (e.g. amount of pAKT in a tumor cell minus amount pAKT in the cell or in a non-tumorous cell of the same type). The pAKT profile can also be expressed in terms of the level of activation of the pathway by measuring amounts of phosphorylated downstream targets of AKT (for example, pGSK or PRAS40). A high pAKT refers to activation or phosphorylation levels of overall AKT in the sample that are higher than a baseline value. In one example, the baseline value is the basal levels of pAKT for a given cell type. In another example, the baseline value is average or mean level of pAKT in a given population of sample cells, for example non-cancerous or cells. In another example, a high pAKT refers to a tumor cell that over-expresses or -amplified phosphorylated or activated AKT in the cell, when compared to an average of normal, healthy (e.g. non-tumorous) cells of the same type from either the same mammal or a patient population. The pAKT profile can also be used in conjunction with other markers, for example FOXO3a localization profiles, for predicting efficacy of certain PI3k/AKT kinase pathway inhibitors, or for example with BRAF V600E mutation status, to predict efficacy of certain combinations of compounds of formula I with vemurafenib, particularly in patients with vemerafenib resistant cancers, such as metastatic or unresectable melanoma. Kits for measuring pAKT in tissue samples are commercially available (e.g. phospho-Akt (Thr308) STAR ELISA kit, EMD Millipore).

Kits for testing for the presence of PI3k, KRAS and AKT mutations are commercially available (Qiagen).

In one specific aspect, the invention provides a method for treating a patient having a cancer that is associated with PTEN mutation or loss of expression, AKT mutation or amplification, PI3K mutation or amplification, Her2/ErbB2 mutation or amplification, KRAS mutation or amplification, BRAF mutation or amplification or a combination thereof comprising administering a combination of the invention to the patient. In another aspect, the invention provides a method for identifying a patient having a cancer that that can be treated with a combination of the invention comprising determining if the patient's cancer is associated with PTEN mutation or loss of expression, AKT mutation or amplification, PI3K mutation or amplification, or Her2/ErbB2 amplification, KRAS mutation or amplification, BRAF mutation or amplification or a combination thereof, wherein association of the patient's cancer with PTEN mutation or loss of expression, AKT mutation or amplification, PI3K mutation or amplification, or Her2/ErbB2 amplification, KRAS mutation or amplification, BRAF mutation or amplification or a combination thereof is indicative of a cancer that can be treated with a combination of the invention. In a further aspect, the invention provides a method further comprising treating the patient so identified with a combination of the invention. In one embodiment, the cancer is ovarian, breast, melanoma, colon or non-small cell lung cancer.

Articles of Manufacture

In another embodiment of the invention, an article of manufacture, or "kit", containing a compound of formula I or pharmaceutically acceptable salt thereof useful for the treatment of the diseases and disorders described above is provided. In one embodiment, the kit comprises a container and a compound of formula I or pharmaceutically acceptable salt thereof.

The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula I or pharmaceutically acceptable salt thereof, or a formulation thereof which is effective for treating the condition and may have a sterile access port (for example, the container may be an intravenous solution bag or a vial having a stopper pierceable by a hypodermic injection needle). At least one active agent in the composition is a compound of formula I or a pharmaceutically acceptable salt thereof. The label or package insert indicates that the composition is used for treating the condition of choice, such as cancer. In one embodiment, the label or package inserts indicates that the composition comprising a compound of formula I or pharmaceutically acceptable salt thereof can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of a compound of formula I or pharmaceutically acceptable salt thereof, and, if present, the second pharmaceutical formulation. For example, if the kit comprises a first composition comprising a compound of formula I or pharmaceutically acceptable salt thereof and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of formula I or pharmaceutically acceptable salt thereof, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of formula I or pharmaceutically acceptable salt thereof contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a composition of a compound of formula I or pharmaceutically acceptable salt thereof and a second therapeutic agent, i.e. the chemotherapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Specific Aspects of the Invention

In one specific aspect of the invention the hyperproliferative disorder is cancer.

In one specific aspect of the invention the cancer is associated with PTEN mutation.

In one specific aspect of the invention the cancer is associated with AKT mutation, overexpression or amplification.

In one specific aspect of the invention the cancer is associated with PI3K mutation.

In one specific aspect of the invention the cancer is associated with KRAS mutation.

In one specific aspect of the invention the cancer is associated with BRAF mutation.

In one specific aspect of the invention the cancer is associated with a combination of a (1) PTEN, AKT or PI3K mutation, and a (2) KRAS or BRAF mutation. In one example, the cancer is ovarian, breast, melanoma, colon or non-small cell lung cancer.

In one specific aspect of the invention, the cancer is resistant to one or both of GDC-0068 and GDC-0973 single agent therapy, but responsive to the combination GDC-0068 and GDC-0973 therapy. In one example, the cancer is ovarian, breast, melanoma, colon or non-small cell lung cancer.

In one specific aspect of the invention the cancer is selected from, mesothelioma, endometrial, pancreatic, breast, lung, ovarian, prostate (e.g. castration resistant prostate cancer), melanoma, gastric, colon, renal, head and neck, and giloma.

In one specific aspect of the invention the compound of formula I or a pharmaceutically acceptable salt thereof is administered orally.

In one specific aspect of the invention the compound of formula I or a pharmaceutically acceptable salt thereof is administered in combination with GDC-0973 or PD-0325901 or a pharmaceutically acceptable salt thereof.

In one specific aspect of the invention the compound of formula I or a pharmaceutically acceptable salt thereof is administered in combination with GDC-0973 or PD-0325901 or a pharmaceutically acceptable salt thereof and the cancer is pancreatic.

In one specific aspect of the invention the compound of formula I or a pharmaceutically acceptable salt thereof is administered in combination with GDC-0973 or a pharmaceutically acceptable salt thereof and the cancer is pancreatic.

In one specific aspect of the invention the compound of formula I or a pharmaceutically acceptable salt thereof is administered in combination with GDC-0973 or PD-0325901 or a pharmaceutically acceptable salt thereof and the cancer is colon.

In one specific aspect of the invention the compound of formula I or a pharmaceutically acceptable salt thereof is administered in combination with GDC-0973 or PD-0325901 or a pharmaceutically acceptable salt thereof and the cancer is breast.

In one specific aspect of the invention the compound of formula I or a pharmaceutically acceptable salt thereof is administered in combination with GDC-0973 or PD-0325901 or a pharmaceutically acceptable salt thereof and the cancer is ovarian.

In one specific aspect of the invention the compound of formula I or a pharmaceutically acceptable salt thereof is administered in combination with GDC-0973 or PD-0325901 or a pharmaceutically acceptable salt thereof and the cancer is lung.

In one specific aspect of the invention the compound of formula I or a pharmaceutically acceptable salt thereof is administered in combination with GDC-0973 or PD-0325901 or a pharmaceutically acceptable salt thereof and the cancer is melanoma.

In one specific aspect of the invention the compound of formula I or a pharmaceutically acceptable salt thereof is formulated as a tablet.

EXAMPLES

In order to illustrate the invention, the following examples are included. However, it is to be understood that these examples do not limit the invention and are only meant to suggest a method of practicing the invention.

Example 1

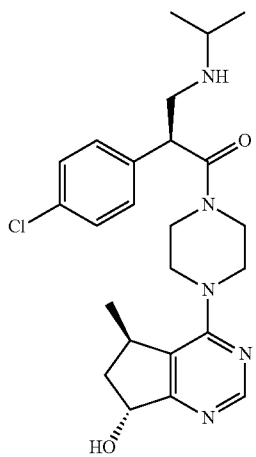

(S)-2-(4-chlorophenyl)-1-(4-((5R,7R)-7-hydroxy-5-methyl-6,7-dihydro-5H-cyclopenta[d]pyrimidin-4-yl)piperazin-4-yl)-3-(isopropylamino)propan-1-one Step 1:

Ethyl pulegenate (130 g, 662 mmol) in EtOAc (900 mL) was cooled to −78° C. using a dry ice-isopropanol bath. This mixture was subjected to ozonolysis until the reaction turned purple in color. At this point, ozone generation ceased, and the reaction was removed from the dry-ice bath. Oxygen was bubbled through the reaction mixture until it turned yellow. The reaction mixture was concentrated under vacuum, and the resulting residue was dissolved in glacial acetic acid (400 mL). The solution was cooled to 0° C., and Zn dust (65 g, 993 mmol) was added portionwise over 30 minutes. The reaction was then allowed to stir for 2 hours, at which point the reaction mixture was filtered through a pad of celite to remove the zinc dust. The acetic acid was neutralized to pH 7 with aqueous NaOH and NaHCO$_3$ and extracted with ether (3×800 mL). The combined organics were dried with brine, MgSO$_4$ and concentrated to give (2R)-ethyl 2-methyl-5-oxocyclopentane-carboxylate as a brown liquid (107 g, 95%).

Step 2:

Ammonium acetate (240.03 g, 3113.9 mmol) was added to a solution of (R)-ethyl 2-methyl-5-oxocyclopentanecarboxylate (106.0 g, 622.78 mmol) in MeOH (1.2 L). The reaction mixture was stirred at room temperature under nitrogen for 20 hours, after which it was complete as judged by TLC and HPLC. The reaction mixture was concentrated to remove MeOH. The resulting residue was dissolved in DCM, washed twice with H$_2$O, once with brine, dried (Na$_2$SO$_4$), filtered, and concentrated to give (R)-ethyl 2-amino-5-methylcyclopent-1-enecarboxylate (102 g, 97% yield) as an orange oil. LC/MS (APCI+) m/z 170 [M+H]$^+$.

Step 3:

A solution containing (R)-ethyl 2-amino-5-methylcyclopent-1-enecarboxylate (161.61 g, 955.024 mmol) and ammonium formate (90.3298 g, 1432.54 mmol) in formamide (303.456 ml, 7640.19 mmol) was heated to an internal temperature of 150° C. and stirred for 17 hours. The reaction mixture was cooled, and transferred to a 2 L single neck flask. Then excess formamidine was removed by high vacuum distillation. Once formamidine stopped coming over, the remaining oil in the still pot was dissolved in DCM and washed with brine (3×200 mL). The combined aqueous washes were extracted with DCM. The combined organic extracts were dried (Na$_2$SO$_4$), filtered, and concentrated. The resulting brown oil was dissolved in minimal DCM, and this solution was added using a separatory funnel to a stirred solution of ether (ca. 5 vol of ether vs. DCM solution), causing some brown precipitate to form. This brown precipitate was removed by filtration through a medium frit funnel which was rinsed with ether and disposed. The filtrate was concentrated, the trituration from ether repeated two more times and then dried on high vacuum line to give (R)-5-methyl-6,7-dihydro-5H-cyclopenta[d]pyrimidin-4-ol (93.225 g, 65.00% yield) as a brown-yellow pasty solid. LC/MS (APCI−) m/z 149.2.

Step 4:

Neat POCl$_3$ (463.9 ml, 5067 mmol) was added slowly by addition funnel to a 0° C. solution of (R)-5-methyl-6,7-dihydro-5H-cyclopenta[d]pyrimidin-4-ol (152.2 g, 1013 mmol) in DCE (1.2 L). After the addition was complete, the reaction mixture was warmed to room temperature, then heated to reflux and stirred for 70 minutes. The reaction was complete as determined by HPLC. The reaction mixture was cooled to room temperature, and the excess POCl$_3$ was quenched in 4 portions as follows: Reaction mixture transferred to separatory funnel and dripped into a beaker containing ice and saturated NaHCO$_3$ solution cooled in an ice bath. Once the addition of each portion of the reaction mixture was completed, the quenched mixture was stirred 30 minutes to ensure complete destruction of POCl$_3$ prior to transfer to separatory funnel. The mixture was transferred to the separatory funnel and extracted twice with DCM. The combined extracts were dried (Na$_2$SO$_4$), filtered, and concentrated. The crude was purified on silica gel as follows: silica gel (1 kg) was slurried in 9:1 hexane:ethyl acetate onto a 3 L fritted funnel, silica settled under vacuum, topped with sand. The crude was loaded with a DCM/hexane mixture, and the compound was eluted using 1 L sidearm flasks under vacuum. High Rf byproducts eluted first, then (R)-4-chloro-5-methyl-6,7-dihydro-5H-cyclopenta[d]pyrimidine (104.4 g, 61.09% yield) as a brown oil. Triethylamine (93.0 ml, 534 mmol) and tert-butyl piperazine-1-carboxylate (34.8 g, 187 mmol) was added to a solution of (R)-4-chloro-5-methyl-6,7-dihydro-5H-cyclopenta[d]pyrimidine (30.0 g, 178 mmol) in n-BuOH (250 mL). The reaction mixture was heated to reflux under nitrogen and stirred overnight (17 hours), after which it was concentrated on a rotavap. The resulting oil was dissolved in DCM, washed with H$_2$O, dried (Na$_2$SO$_4$), filtered, and was concentrated. The resulting brown oil was purified on silica gel eluting first with 2:1 hexanes:ethyl acetate until product eluting cleanly, then gradient 1:1 to 1:5 DCM:ethyl acetate to give (R)-tertbutyl 4-(5-methyl-6,7-dihydro-5H-cyclopenta[d]pyrimidin-4-yl)piperazine-1-carboxylate (42.0 g, 74.1% yield) as a beige powder. LC/MS (APCI+) m/z 319.1 [M+H]$^+$.

Step 5:

Solid 77% max. MCPBA (23.9 g, 107 mmol) was added portionwise to a 0° C. solution of (R)-tert-butyl 4-(5-methyl-6,7-dihydro-5H-cyclopenta[d]pyrimidin-4-yl)piperazine-1-carboxylate (20.0 g, 62.8 mmol) in CHCl$_3$ (310 mL). The reaction mixture was stirred 5 for minutes, then warmed to room temperature and stirred for 90 minutes. HPLC looked similar after 7.5 hours. The reaction mixture was cooled to 0° C., then NaHCO$_3$ (13.2 g, 157 mmol) and another 0.5 equivalents of m-CPBA were added. The reaction mixture was stirred overnight (14 hours). The reaction mixture was cooled to 0° C., and a solution of Na$_2$S$_2$O$_3$ (29.8 g, 188 mmol) in H$_2$O (50 mL) was added dropwise by addition funnel. This was followed by a solution of Na$_2$CO$_3$ (24.6 g, 232 mmol) in H$_2$O (70 mL) by addition funnel (mixture turns homogeneous). The reaction mixture was stirred for 30 minutes, then the mixture was extracted with CHCl$_3$ (3×150 mL). The combined extracts were dried (Na$_2$SO$_4$), filtered, and concentrated to give the N-oxide. LC/MS (APCI+) m/z 335.1 [M+H]$^+$.

Step 6:

Ac$_2$O (77.0 ml, 816 mmol) was added to the N-oxide (21.0 g, 62.8 mmol) from Step 5. The reaction mixture was heated under nitrogen in a 90° C. sand bath and stirred for 100 minutes. The reaction mixture was cooled to room temperature, and excess acetic anhydride was removed by rotary evaporation. The resulting oil was dissolved in DCM, which was then poured carefully into ice saturated Na$_2$CO$_3$. The mixture was extracted with DCM, and the combined extracts were dried (Na$_2$SO$_4$), filtered, and concentrated to give (5R)-tert-butyl 4-(7-acetoxy-5-methyl-6,7-dihydro-5H-cyclopenta[d]pyrimidin-4-yl)piperazine-1-carboxylate (23.6 g, 100%) as a brown foam. LC/MS (APCI+) m/z 377.1 [M+H]$^+$.

Step 7:

LiOH—H$_2$O (6.577 g, 156.7 mmol) was added to a 0° C. solution of (5R)-tert-butyl 4-(7-acetoxy-5-methyl-6,7-dihydro-5H-cyclopenta[d]pyrimidin-4-yl)piperazine-1-carboxylate (23.6 g, 62.69 mmol) in 2:1 THF:H$_2$O (320 mL). The reaction mixture was stirred for 10 minutes, and then warmed to room temperature. LC/MS looked the same at 3 hours and 4.5 hours. The reaction mixture was cooled to 0° C., and then saturated NH$_4$Cl was added to the mixture. The mixture was stirred for 5 minutes, and most of the THF was removed by rotary evaporation. The mixture was extracted with EtOAc (3×250 mL), and the combined extracts were dried (Na$_2$SO$_4$), filtered, and concentrated. The crude was flashed on Biotage 65M: 4:1 DCM:ethyl acetate, then gradient to 1:1 to 1:4 DCM:ethyl acetate. Once the product was eluting, then ethyl acetate was flushed through the column. Then 30:1 DCM:MeOH eluted the rest of the product (8.83 g). The mixed fractions were re-flashed with Biotage 40M using the same conditions to give another 2.99 g which gave a combined yield of (5R)-tert-butyl 4-(7-hydroxy-5-methyl-6,7-dihydro-5H-cyclopenta[d]pyrimidin-4-yl)piperazine-1-carboxylate (11.82 g, 56.38% yield) as a brown foam. LC/MS (APCI+) m/z 335.1 [M+H]$^+$.

Step 8:

A solution of DMSO (5.45 ml, 76.8 mmol) in DCM (50 mL) was added dropwise by addition funnel to a −78° C. solution of oxalyl chloride (3.35 ml, 38.4 mmol) in DCM (150 mL). The reaction mixture was stirred for 35 minutes, and then a solution of (5R)-tert-butyl 4-(7-hydroxy-5-methyl-6,7-dihydro-5H-cyclopenta[d]pyrimidin-4-yl)piperazine-1-carboxylate (9.17 g, 27.4 mmol) in DCM (80 mL) was added slowly by addition funnel. The reaction mixture was stirred another 1 hour at −78° C., after which neat triethylamine (18.0 ml, 129 mmol) was added to the mixture. The reaction mixture was then allowed to warm to room temperature, and then it was stirred for 30 minutes. H$_2$O was added. The mixture was extracted with DCM (3×200 mL), and the combined extracts were dried (Na$_2$SO$_4$), filtered, and concentrated in vacuo. The crude was purified on silica gel (Biotage 65M): the column was flushed with ca. 800 mL 4:1 DCM:EtOAc, then gradient to 1:1 DCM:ethyl acetate until product eluting, then 1:4 DCM:EtOAc eluted product to give (R)-tert-butyl 4-(5-methyl-7-oxo-6,7-dihydro-5H-cyclopenta[d]pyrimidin-4-yl)piperazine-1-carboxylate (7.5 g, 82.3% yield) as a brown foam. The foam was concentrated (3×) from DCM/hexanes, which gave a very light brown foam. HPLC >95% area. LC/MS (APCI+) m/z 333 [M+H]$^+$.

Step 9:

Triethylamine (4.33 ml, 31.1 mmol; degassed with nitrogen 30 minutes prior to use) and formic acid (1.36 ml, 36.1 mmol; degassed with nitrogen 30 minutes prior to use) were added to a solution of (R)-tert-butyl 4-(5-methyl-7-oxo-6,7-dihydro-5H-cyclopenta[d]pyrimidin-4-yl)piperazine-1-carboxylate (9.75 g, 29.3 mmol) in DCM (210 mL; degassed with nitrogen 30 minutes prior to use). The mixture was stirred for 5 minutes, then a Ru catalyst (0.0933 g, 0.147 mmol) was added. The reaction was stirred under positive nitrogen pressure overnight (18 hours). The reaction mixture was concentrated to dryness and dried on high vacuum. The impure material was flashed on Biotage 65M loaded 1:1 DCM:ethyl acetate 500 mL flushed, then 1:4 DCM:ethyl acetate until product (2nd spot), then gradient to neat ethyl acetate, then 25:1 DCM:MeOH eluted rest of product. The fractions were combined and concentrated on a rotary evaporator. The residue was concentrated again from DCM/hexanes to give a mixture of tert-butyl 4-((5R,7R)-7-hydroxy-5-methyl-6,7-dihydro-5H-cyclopenta[d]pyrimidin-4-yl)piperazine-1-carboxylate (major) and tert-butyl 4-((5R,7S)-7-hydroxy-5-methyl-6,7-dihydro-5H-cyclopenta[d]pyrimidin-4-yl)piperazine-1-carboxylate (minor) (9.35 g, 95.3% yield) as a beige foam. LC/MS (APCI+) m/z 335 [M+H]$^+$. $^1$H NMR (CDCl$_3$) shows 88% de by integration of carbinol methine.

Step 10:

4-Nitrobenzoyl chloride (4.27 g, 23.0 mmol) was added to a 0° C. solution of tert-butyl 4-((5R,7R)-7-hydroxy-5-methyl-6,7-dihydro-5H-cyclopenta[d]pyrimidin-4-yl)piperazine-1-carboxylate (7.0 g, 20.9 mmol) and triethylamine (4.38 ml, 31.4 mmol) in DCM (110 mL). The reaction mixture was stirred at room temperature overnight, after which saturated NaHCO$_3$ was added. The mixture was stirred 10 minutes, and then extracted with DCM. The combined extracts were dried (Na$_2$SO$_4$), filtered, and concentrated. The crude was flashed on Biotage 65M (3:1 hexanes:ethyl acetate loaded crude, then 2:1 hexanes:ethyl acetate eluted tert-butyl 4-((5R,7R)-5-methyl-7-(4-nitrobenzoyloxy)-6,7-dihydro-5H-cyclopenta[d]pyrimidin-4-yl)piperazine-1-carboxylate and a few mixed fractions). Then tert-butyl 4-((5R,7S)-5-methyl-7-(4-nitrobenzoyloxy)-6,7-dihydro-5H-cyclopenta[d]pyrimidin-4-yl)piperazine-1-carboxylate was eluted using 1:2 hexanes:ethyl acetate. The fractions with product were concentrated by rotary evaporation to give tert-butyl 4-((5R,7R)-5-methyl-7-(4-nitrobenzoyloxy)-6,7-dihydro-5H-cyclopenta[d]pyrimidin-4-yl)piperazine-1-carboxylate (8.55 g, 84.5% yield) as a yellow foam. LC/MS (APCI+) m/z 484 [M+H]$^+$. $^1$H NMR (CDCl$_3$) shows single diastereomer). The fractions with other diastereomer were concentrated by rotary evaporation to give tert-butyl 4-((5R,7S)-5-methyl-7-(4-nitrobenzoyloxy)-6,7-dihydro-5H-cyclopenta[d]pyrimidin-4-yl)piperazine-1-carboxylate (0.356 g, 3.52% yield) as a brown foam. LC/MS (APCI+) m/z 484 [M+H]$^+$.

Step 11:

LiOH—H$_2$O (0.499 g, 11.9 mmol) was added to a 0° C. solution of tert-butyl 4-((5R,7R)-5-methyl-7-(4-nitrobenzoyloxy)-6,7-dihydro-5H-cyclopenta[d]pyrimidin-4-yl)piperazine-1-carboxylate (2.30 g, 4.76 mmol) in 2:1 THF:H$_2$O (40 mL). The reaction mixture was warmed to room temperature and stirred for 1 hour. The THF was removed by rotary evaporation, saturated NaHCO$_3$ was added, and the mixture was extracted with ethyl acetate. The combined extracts were washed (1×) with saturated NaHCO$_3$, dried (Na$_2$SO$_4$), filtered, and concentrated to give tert-butyl 4-((5R,7R)-7-hydroxy-5-methyl-6,7-dihydro-5H-cyclopenta[d]pyrimidin-4-yl)piperazine-1-carboxylate (1.59 g, 100.0% yield) as a yellow foam. HPLC after workup just product >98 area % pure. LC/MS (APCI+) m/z 335 [M+H]$^+$. The tert-butyl 4-((5R,7S)-7-hydroxy-5-methyl-6,7-dihydro-5H-cyclopenta[d]pyrimidin-4-yl)piperazine-1-carboxylate was prepared using an analogous method.

Step 12:

4M HCl/dioxane (11.2 ml, 44.9 mmol) was added to a solution of tert-butyl 4-((5R,7R)-7-hydroxy-5-methyl-6,7-dihydro-5H-cyclopenta[d]pyrimidin-4-yl)piperazine-1-carboxylate (0.600 g, 1.79 mmol) in dioxane (15 mL). The reaction mixture was stirred at room temperature under nitrogen overnight (20 hours). The mixture was concentrated to dryness and dried on high vacuum line. The crude was suspended in ether, sonicated, and stirred for 5 minutes. The solids were isolated by filtration through a medium frit funnel with nitrogen pressure, rinsed with ether, dried under nitrogen pressure, and dried further on a hi vacuum line to give (5R,7R)-5-methyl-4-(piperazin-1-yl)-6,7-dihydro-5H-cyclopenta[d]pyrimidin-7-ol dihydrochloride (0.440 g, 79.8% yield) as a yellow powder. LC/MS (APCI+) m/z 235. The (5R,7S)-5-methyl-4-(piperazin-1-yl)-6,7-dihydro-5H-cyclopenta[d]pyrimidin-7-ol dihydrochloride was prepared using an analogous method.

Step 13:

Methyl 2-(4-chlorophenyl)acetate (36.7 g, 199 mmol) and paraformaldehyde (6.27 g, 209 mmol) were dissolved/suspended in DMSO (400 mL) and treated with NaOMe (537 mg, 9.94 mmol). The mixture was allowed to stir at room temperature for 2 hours to completion by TLC analysis of the crude. The reaction was poured into ice-cold water (700 mL; white emulsion) and neutralized with the addition of 1M HCl solution. The aqueous layer was extracted with ethyl acetate (3×), and the organics were combined. The organic layer was washed with water (2×), brine (1×), separated, dried over MgSO$_4$, filtered, and concentrated in vacuo to afford the crude product as a yellow oil. The residue was loaded onto a large fritted filtered with silica gel and eluted with 9:1 hexanes:ethyl acetate until the starting material/olefin were collected. The plug was then eluted with 1:1 hexanes:ethyl acetate until the pure desired product was eluted completely. The concentrated pure fractions yielded methyl 2-(4-chlorophenyl)-3-hydroxypropanoate as a colorless oil (39.4 g, 92%).

Step 14:

Methyl 2-(4-chlorophenyl)-3-hydroxypropanoate (39.4 g, 184 mmol) was dissolved in DCM (500 mL) and treated with TEA (64.0 mL, 459 mmol). The solution was cooled to 0° C. and slowly treated with MsCl (15.6 mL, 202 mmol), then allowed to stir for 30 minutes to completion by TLC analysis. The solution was partitioned with 1N HCl solution, and the aqueous layer was extracted once with DCM. The combined organic layer was washed once more with 1N HCl solution, separated, washed with diluted NaHCO$_3$ solution, and separated. The organic layer was dried over MgSO$_4$, filtered, and concentrated in vacuo to afford an orange oil. The residue was loaded onto a large fritted filter with a plug of silica gel and eluted with 9:1 hexanes:ethyl acetate affording the pure desired product by TLC analysis. The concentrated pure fractions yielded the methyl 2-(4-chlorophenyl)acrylate as a colorless oil (30.8 g, 85%). This methyl 2-(4-chlorophenyl)acrylate (500 mg, 2.54 mmol) was added as a solution in THF (1.35 mL) to a stirring solution of i-PrNH$_2$ (217 uL, 2.54 mmol) in THF (5.0 mL) at 0° C. The reaction was allowed to stir at room temperature overnight to completion by LCMS analysis. The Boc2O (584 uL, 2.54 mmol) was added to the stirring amine via pipet. The reaction was allowed to stir overnight to completion by LCMS and TLC analysis of the mixture. The solution was concentrated in vacuo to afford methyl 3-(tert-butoxycarbonyl(isopropyl)amino)-2-(4-chlorophenyl)propanoate as a colorless oil (854 mg, 94%). LC/MS (APCI+) m/z 256.1 [M-Boc]+.

Step 15:

Methyl 3-(tert-butoxycarbonyl(isopropyl)amino)-2-(4-chlorophenyl)propanoate (133 g, 374 mmol) was dissolved in THF (1.0 L) and treated with KOTMS (56.0 g, 392 mmol) at room temperature. The mixture was allowed to stir overnight to completion by LCMS analysis of the crude. The mixture was concentrated in vacuo to afford a wet foam, which was allowed to dry under vacuum overnight to afford potassium 3-(tert-butoxycarbonyl(isopropyl)amino)-2-(4-chlorophenyl)propanoate as a white solid (148.7 g, 105%). LC/MS (APCI+) m/z 242.1 [M-Boc-K]+.

Step 16:

Potassium 3-(tert-butoxycarbonyl(isopropyl)amino)-2-(4-chlorophenyl)propanoate (77.2 g, 203 mmol) was dissolved in THF (515 mL) and treated with pivaloyl chloride (26.3 mL, 213 mmol) at room temperature. The mixture was allowed to stir for 3 hours to form the mixed anhydride. (S)-4-benzyloxazolidin-2-one (46.1 g, 260 mmol) was dissolved in THF (600 mL) and cooled to −78° C. in a separate flask. The solution was treated with n-BuLi (102 mL of a 2.50M solution in hexanes, 254 mmol) and allowed to stir for one hour. The prepared anhydride solution was added to the stirring Li-oxazolidinone via cannula, and the mixture was allowed to warm to room temperature overnight. The mixture was quenched with the addition of saturated ammonium chloride solution, then partitioned between more water and ethyl acetate. The aqueous layer was extracted several times, and the organics were combined. The organic layer was washed with water, then brine, separated, dried over MgSO$_4$, filtered, and concentrated in vacuo. The residue was purified/separated (diastereomers) via chromatography (silica gel eluted with 4:1 hexanes:ethyl acetate) to afford the completely separated diastereomers as viscous oils: tert-butyl (R)-3-(S)-4-benzyl-2-oxooxazolidin-3-yl)-2-(4-chlorophenyl)-3-oxopropyl(isopropyl)carbamate (12.16 g, 24% based on ½ of acid racemate) and tert-butyl (S)-3-(S)-4-benzyl-2-oxooxazolidin-3-yl)-2-(4-chlorophenyl)-3-oxopropyl(isopropyl)carbamate (39.14 g, 77% based on ½ of acid racemate). LC/MS (APCI+) m/z 401.2 [M-Boc]+.

Step 17:

LiOH—H$_2$O (168 mg, 4.00 mmol) was added to a stirring solution of THF (30 mL) and water (15 mL) at room temperature until it was dissolved. The mixture was treated with hydrogen peroxide (658 uL of a 35% wt. solution in water, 8.00 mmol) and allowed to stir at room temperature for 10 minutes. The reaction was cooled to 0° C. in an ice bath, and the tert-butyl (S)-3-(S)-4-benzyl-2-oxooxazolidin-3-yl)-2-(4-chlorophenyl)-3-oxopropyl(isopropyl)carbamate (1.00 g, 2.00 mmol) was added dropwise via addition funnel as a solution in THF (15 mL) over a 10 minutes. The mixture was allowed to stir overnight at room temperature to completion by LCMS analysis of the crude. The reaction was cooled to 0° C., and then treated with 1M Na$_2$SO$_3$ (9.00 mL) solution via addition funnel over a ten minute period. After the addition was complete, the mixture was allowed to warm to room temperature for 10 minutes. The mixture was concentrated to remove the THF, and then diluted with water. The aqueous layer was washed twice with ethyl acetate (discarded). The aqueous layer was partitioned with ethyl acetate, then treated dropwise while stirring with 1M HCl until pH 2-3 was attained. The aqueous layer was extracted twice with ethyl acetate, and the organics were combined. The organic was washed with brine, separated, dried over MgSO$_4$, filtered, and concentrated in vacuo. The colorless oil product was dried under high vacuum for one hour to afford (S)-3-(tert-butoxycarbonyl(isopropyl)amino)-2-(4-chlorophenyl)propanoic acid as a viscous oil/foam (685 mg, 100%). LC/MS (APCI+) m/z 242.1 [M-Boc]+.

Step 18:

A solution of (5R,7R)-5-methyl-4-(piperazin-1-yl)-6,7-dihydro-5H-cyclopenta[d]pyrimidin-7-ol dihydrochloride (2.92 g, 9.51 mmol) and (S)-3-(tert-butoxycarbonyl(isopropyl)amino)-2-(4-chlorophenyl)propanoic acid (3.25 g, 9.51 mmol) in DCM (40 mL) and DIEA (5.0 mL, 28.7 mmol) was stirred at room temperature for 10 minutes. HBTU (3.61 g, 9.51 mmol) was added to the mixture. The mixture was stirred at room temperature for 1 hour. The solvent was removed, and the residue was dissolved in ethyl acetate (500 mL) and washed with water (6×100 mL). The organic phase was dried and concentrated. The residue was subject to column chromatography, eluted by EtOAc-DCM/MeOH (20:1) to give tert-butyl (S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl(isopropyl)carbamate (3.68 g, 69%.) LC/MS (APCI+) m/z 558.2 [M+H]$^+$.

Step 19:

The tert-butyl (S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl(isopropyl) carbamate (2.50 g, 4.48 mmol) was dissolved in dioxane (22.4 mL) and treated with 4M HCl in dioxane (22.4 mL, 89.6 mmol) at room temperature. The resulting solution was allowed to stir overnight to completion by LCMS analysis of the crude. The solution was concentrated in vacuo to afford a gel that was dissolved in a minimal amount of methanol (10 mL). The solution was transferred via pipette to stirred ether (300 mL) to afford a white precipitate of desired product. The addition was about half when the white precipitate melted into a yellow gel. The material was concentrated in vacuo to afford a yellow gel which was allowed to stand under reduced pressure overnight to yield (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one dihydrochloride as a light yellow powder (2.14 g, 90%). $^1$H NMR (D$_2$O, 400 MHz☐☐☐☐8.39 (s, 1H), 7.37-7.35 (d, J=8.4 Hz, 2H), 7.23-7.20 (d, J=8.4 Hz, 2H), 5.29-5.25 (m, 1H), 4.33-4.29 (m, 1H), 4.14-4.10 (m, 1H), 3.89-3.19 (m, 11H), 2.23-2.17 (m, 1H), 2.08-1.99 (m, 1H), 1.20-1.18 (m, 6H), 0.98-0.96 (d, J=6.8 Hz, 3H). MS (APCI+) [M+H]$^+$ 458.

Example 2

In Vitro Cell Proliferation Assays

The in vitro potency of the combinations of the compound of formula I with certain specific chemotherapeutic agents can be measured using the CellTiter-Glo® Luminescent Cell Viability Assay, commercially available from Promega Corp., Madison, Wis. This homogeneous assay method is based on the recombinant expression of Coleoptera luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay can be conducted in 96 or 384 well format, making it amenable to automated high-throughput screening (HTS) (Cree et al (1995) Anti-Cancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

Example 3 In Vivo Tumor Xenograft Efficacy

The efficacy of representative combinations of the invention were measured in vivo by implanting allografts or xenografts of cancer cells in rodents and treating the tumor-bearing animals with the combinations. Variable results are to be expected depending on the cell line, the presence or absence of certain mutations in the tumor cells, the sequence of administration the compounds, dosing regimen, and other factors. Subject mice were treated with drug(s) or control (Vehicle) and monitored over several weeks or more to measure the time to tumor doubling, log cell kill, and tumor inhibition. Results for representative combinations of the invention that were tested in this model are presented in the Figures. The data in the Figures demonstrates that representative combinations provide improved results compared to the administration of the respective agents individually.

Example 4 Measuring PTEN Status

PTEN status may be measured by any suitable means as is known in the art. In one example, IHC is used. Alternatively, Western blot analysis can be used. Antibodies to PTEN are commercially available (Cell Signaling Technology, Beverly, Mass., Cascade Biosciences, Winchester, Mass.). Example procedures for IHC and Western blot analysis for PTEN status are described in Neshat, M. S. et al. Enhanced sensitivity of PTEN-deficient tumors to inhibition of FRAP/mTOR, Proc. Natl. Acad. Sci. USA 98, 10314-10319 (2001) and Perren, A., et. al. Immunohistochemical Evidence of Loss of PTEN Expression in Primary Ductal Adenocarcinomas of the Breast, American Journal of Pathology, Vol. 155, No. 4, October 1999. Additionally, cancers associated with AKT mutation, PI3K mutation, and with Her2/ErbB2 amplification can be identified using techniques that are known in the art.

Example 5 Cell Viability Assays

Cells were plated in black, clear-bottomed 384-well plates (Catalog 353962; Becton Dickinson; Franklin Lakes, N.J.) at a density of 1500 cells/well and incubated overnight to 1.5 days at 37° C., 5% $CO_2$. Serial dilutions of GDC-0068, GDC-0973, or both in combination were then added to the cells and incubated for another 96 hours. Cell viability was determined by measuring the cellular adenosine triphosphate (ATP) levels as described in the manufacturer's protocol (CellTiter-Glo Luminescent Cell Viability Assay kit; Catalog G7573; Promega, Madison, Wis.). Luminescence signal was recorded on an EnVision 2101 Multilabel Reader (PerkinElmer; Waltham, Mass.).

Percentage inhibition was calculated by dividing the relative light unit (RLU) of cells exposed to the GDC-0068 and GCD-0973 combination to the RLU of cells exposed to DMSO and subtracting it from 1, as expressed below:

% inhibition=1−($RLU_{combination}$/$RLU_{DMSO}$)

BLISS analysis compared the expected % inhibition ($E=E_{GDC-0068}+E_{GDC-0973}-E_{GDC-0068} \times E_{GDC-0973}$) with the experimentally observed % inhibition, $E_{OBS}$. The BLISS score is the difference ($\Delta E=E_{OBS}-E$) between the expected % inhibition, E, and the experimentally observed inhibition, $E_{OBS}$.

BLISS scores quantify degree of potentiation from single agents and a positive BLISS score suggests greater than simple additivity. A total BLISS score greater than 250 is considered strong synergy observed within the concentration ranges tested.

Examples of combination potencies are shown as heatmaps in three cancer cell lines: A2058, a melanoma cell line with PTEN deficiency and B-RAF$^{V600E}$ mutation (see FIG. 9); HCT-116, a colorectal cancer (CRC) cell line with PIK3CA$^{H1047R}$ and KRAS$^{G13D}$ mutations (see FIG. 5); and NCI-H2122, a non-small cell lung cancer (NSCLC) cell line with a KRAS$^{G12C}$ mutation (see FIG. 7). Strong synergistic effects with BLISS scores ≥15 for individual dose pairs were observed at GDC-0068 concentrations between 0.37 and 10 µM and GDC-0973 concentrations between 0.062 and 0.56 µM in all three cell lines.

To further investigate whether the synergistic effect between GDC-0068 and GDC-0973 is dependent on activation of the RAS/RAF and/or the PI3K/Akt pathways, the combination effects were compared in a set of cell lines derived from a melanoma patient: the MALME3M B-RAF$^{V600E}$ metastatic melanoma cell line and the patient-matched MALME3 normal skin fibroblasts. MALME3M cells showed sensitivity to GDC-0973 at low concentrations, and strong synergistic effect was also observed at low concentrations of GDC-0973 and a wide range of GDC-0068 concentrations despite the lack of single agent activity of GDC-0068 (see FIG. 28). In contrast, MALME3 cells were resistant to GDC-0973 and no synergism was observed in combination with GDC-0068 (see FIG. 29). Similarly, NCI-BL2122, normal B lymphoblasts derived from the same patient as the NSCLC cell line NCI-H2122, also displayed no synergistic response to the combination of GDC-0973 and GDC-0068 (see FIG. 30), in contrast to the strong synergy in the NCI-H2122 cells (see FIG. 7). These results suggest that a therapeutic benefit with combinations of MEK and Akt inhibitors may be selectively observed in cancer cells in which either the RAS/RAF pathway or both PI3K/Akt and RAS/RAF pathways are active.

Example 6 Western Blot Analysis

Dishes (10 cm$^2$) were seeded with two million cells in a volume of 10 mL followed by incubation at 37° C. under 5% $CO_2$ overnight (approximately 16 hours). Cells were exposed to 1 and 3 µM of GDC-0068, 0.25 and 0.75 µM GDC-0973, or 1 µM GDC-0068 plus 0.25 µM GDC-0973 for 3 hours. Following exposure, cells were washed with cold phosphate-buffered saline (PBS) and lysed in 1× Cell Extraction Buffer from Biosource (Carlsbad, Calif.) supplemented with protease inhibitors (Roche, Germany), 1 mM phenylmethanesulfonyl fluoride (PMSF), and Phosphatase Inhibitor Cocktails 1 and 2 from Sigma (St. Louis, Mo.). Protein concentration was determined using the Bradford method (Bio-Rad Protein Assay (Bio-Rad; Hercules, Calif.). For immunoblots, equal protein amounts were separated by electrophoresis through Tris-Glycine 4-20% gradient gels (Invitrogen; Carlsbad, Calif.); proteins were transferred onto nitrocellulose membranes using the Criterion system and protocol from Bio-Rad.

The following antibodies, all from Cell Signaling Technologies (Beverly, Mass.), unless otherwise specified, were used:
    anti-pAkt (S473)
    anti-pAkt (T308)
    anti pMEK1/2 (S217/221)
    anti-pFoxO1 (T24)/FoxO3a (T32)
    anti-pPRAS40 (T246)
    anti-p4EBP1 (T37/46)
    anti-pERK1/2 (T202/Y204)
    anti-pTSC2 (T1462)
    anti-pS6 (S235/236)
    anti-pS6 (S240/244)
    poly (ADP-ribose) polymerase (PARP) and cleaved PARP
    GAPDH (from Advanced ImmunoChemical; Long Beach, Calif.)

To investigate the effect of the combination on Akt and MEK signaling, downstream targets of both Akt and MEK were evaluated by Western blots in HCT-116 CRC cells exposed to GDC-0068 at 1 and 3 µM, GDC-0973 at 0.25 and 0.75 µM, or GDC-0068 at 1 µM in combination with GDC-0973 at 0.25 µM, where synergistic effect was observed. As shown in FIG. 24, combined knockdown of downstream targets of both Akt and MEK was observed in the combination, with enhanced knockdown of several targets, such as pTSC2, pS6 (both s235/236 and S240/244), PARP and cleaved PARP, showing better knockdown than each single agent alone even at a higher dose.

Example 7 Flow Cytometry Assays

HCT-116 cells were seeded in 96-well tissue culture plates. After overnight incubation at 37° C., 5% $CO_2$, the cells were exposed to either GDC-0068 or GDC-0973 or in combination at increasing concentrations for 4 days. To detect apoptosis, 100 µL of cell suspension was added to 100 µL PBS containing 4 mM $CaCl_2$, 5 µL annexin V-fluorescein isothiocyanate (FITC) (BD Pharmingen; Franklin Lakes, N.J.), and 5 µg/mL propium iodide (PI). The mixture was incubated on ice for 30 minutes and cells were analyzed with a flow cytometer (BD Biosciences; San Jose, Calif.).

Percentage of propidium iodide- (PI) or annexin V- (AV) positive cells was measured at each single agent or combination pair of GDC-0068 and GDC-0973, and synergistic effect of cell death induction was analyzed by BLISS analysis. The combination resulted in increased percentage of PI+/AV+ cells compared with each single agent alone, with strong synergistic effect (BLISS score ≥15) observed at 0.37 to 10 μM of GDC-0068 and 0.185 to 0.556 μM of GDC-0973. Therefore, combination between GDC-0068 and GDC-0973 also resulted in synergistic effect on cell death induction in HCT-116 cells.

Further, since numerous modifications and changes will be readily apparent to those skilled in the art, it is not desired to limit the invention to the exact construction and process shown as described above. Accordingly, all suitable modifications and equivalents may be considered to fall within the scope as defined by the claims that follow.

We claim:

1. A method for treating melanoma in a mammal, comprising administering to the mammal a combination of a compound of formula I:

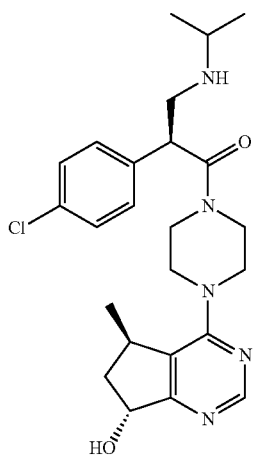 [SMILES: CC(C)NC[C@@H](C(=O)N1CCN(c2ncnc3c2[C@H](C)C[C@H]3O)CC1)c1ccc(Cl)cc1]

(I)

or a pharmaceutically acceptable salt thereof; and an agent selected from GDC-0973 or a pharmaceutically acceptable salt thereof, wherein the combination is present in an amount effective to provide a synergistic effect in treating the melanoma, wherein the combination is present at a ratio of from 1:1 to 16:1 of the compound of formula I or a pharmaceutically acceptable salt thereof: GDC-0973 or a pharmaceutically acceptable salt thereof.

2. The method of claim 1, wherein the melanoma is associated with PTEN mutation.

3. The method of claim 1, wherein the melanoma is associated with AKT mutation, overexpression or amplification.

4. The method of claim 1, wherein the melanoma is associated with PI3K mutation.

5. The method of claim 1, wherein the melanoma is associated with Her2/ErbB2 amplification.

6. The method of claim 1, wherein the compound of formula I or the salt thereof is administered simultaneously with the GDC-0973 or a pharmaceutically acceptable salt thereof.

7. The method of claim 1, wherein the compound of formula I or the salt and the GDC-0973 or a pharmaceutically acceptable salt thereof are administered sequentially.

8. The method of claim 1, wherein administration of the GDC-0973 or a pharmaceutically acceptable salt thereof begins about 1 to about 10 days before administration of the compound of formula I or the salt.

9. The method of claim 1, wherein administration of the compound of formula I or the salt thereof begins about 1 to about 10 days before administration of the GDC-0973 or a pharmaceutically acceptable salt thereof.

10. The method of claim 1, wherein administration of the compound of formula I or the salt thereof and administration of the GDC-0973 or a pharmaceutically acceptable salt thereof begins on the same day.

* * * * *